(12) United States Patent
Marin et al.

(10) Patent No.: US 12,240,925 B2
(45) Date of Patent: *Mar. 4, 2025

(54) PROCESS FOR PREPARING SOLID CATALYST COMPONENTS FOR OLEFIN POLYMERIZATION

(71) Applicant: W. R. Grace & Co.-Conn., Columbia, MD (US)

(72) Inventors: Vladimir P. Marin, Pasadena, TX (US); Ahmed Hintolay, Pasadena, TX (US)

(73) Assignee: W. R. Grace & Co.- Conn., Columbia, MD (US)

( * ) Notice: Subject to any disclaimer, the term of this patent is extended or adjusted under 35 U.S.C. 154(b) by 195 days.

This patent is subject to a terminal disclaimer.

(21) Appl. No.: 17/824,418

(22) Filed: May 25, 2022

(65) Prior Publication Data

US 2022/0289881 A1    Sep. 15, 2022

Related U.S. Application Data

(63) Continuation of application No. 16/762,331, filed as application No. PCT/US2018/059311 on Nov. 6, 2018, now Pat. No. 11,634,520.

(60) Provisional application No. 62/585,137, filed on Nov. 13, 2017.

(51) Int. Cl.

| | |
|---|---|
| C08F 10/02 | (2006.01) |
| C07C 69/78 | (2006.01) |
| C08F 4/52 | (2006.01) |
| C08F 4/64 | (2006.01) |
| C08F 110/06 | (2006.01) |
| C08F 210/06 | (2006.01) |
| C08F 210/16 | (2006.01) |
| C08L 23/16 | (2006.01) |
| B01J 31/02 | (2006.01) |
| B01J 31/36 | (2006.01) |
| C08F 4/618 | (2006.01) |
| C08F 4/649 | (2006.01) |
| C08F 4/654 | (2006.01) |
| C08F 4/656 | (2006.01) |

(52) U.S. Cl.
CPC ............ C08F 210/06 (2013.01); C07C 69/78 (2013.01); C08F 10/02 (2013.01); C08F 110/06 (2013.01); C08F 210/16 (2013.01); C08L 23/16 (2013.01); B01J 31/0258 (2013.01); B01J 31/36 (2013.01); C08F 4/6183 (2013.01); C08F 4/6186 (2013.01); C08F 4/6497 (2013.01); C08F 4/6543 (2013.01); C08F 4/656 (2013.01); C08F 4/6565 (2013.01); C08F 2410/03 (2013.01); C08F 2500/12 (2013.01); C08F 2500/18 (2013.01); C08F 2500/24 (2013.01); C08F 2800/20 (2013.01); C08L 2207/02 (2013.01)

(58) Field of Classification Search
CPC ........ C08F 210/16; C08F 110/02; B01J 31/36
See application file for complete search history.

(56) References Cited

U.S. PATENT DOCUMENTS

| | | |
|---|---|---|
| 4,784,983 A | 11/1988 | Mao et al. |
| 4,861,847 A | 8/1989 | Mao et al. |
| 5,767,034 A | 6/1998 | Diaz-Barrios et al. |
| 6,376,417 B1 | 4/2002 | Yang et al. |
| 6,403,518 B2 | 6/2002 | Ward |
| 6,469,112 B2 | 10/2002 | Cheng et al. |
| H2060 H | 3/2003 | Spencer et al. |
| 6,683,017 B2 | 1/2004 | Gao et al. |
| 6,703,339 B2 | 3/2004 | Li et al. |
| 7,196,140 B2 | 3/2007 | Dahn et al. |
| 7,332,455 B2 | 2/2008 | Wei et al. |
| 7,351,778 B2 | 4/2008 | Gao et al. |
| 7,388,060 B2 | 6/2008 | Wang et al. |
| 7,893,003 B2 | 2/2011 | Chen |
| 8,003,558 B2 | 8/2011 | Chang |
| 8,067,510 B2 | 11/2011 | Sheard et al. |

(Continued)

FOREIGN PATENT DOCUMENTS

| | | |
|---|---|---|
| BR | 0821495 A2 | 6/2015 |
| CN | 101724105 A | 6/2010 |

(Continued)

OTHER PUBLICATIONS

First Office Action on CO Appln. No. NC2020/0006368 dated Dec. 9, 2022 (including partial English translation, 12 pages).

(Continued)

*Primary Examiner* — Rip A Lee

(74) *Attorney, Agent, or Firm* — DORITY & MANNING, P.A.

(57) ABSTRACT

A process of preparing a solid catalyst component for the production of polypropylene includes a) dissolving a halide-containing magnesium compound in a mixture, the mixture including an epoxy compound, an organic phosphorus compound, and a hydrocarbon solvent to form a homogenous solution; b) treating the homogenous solution with an organosilicon compound during or after the dissolving step; c) treating the homogenous solution with a first titanium compound in the presence of a first non-phthalate electron donor, and an organosilicon compound, to form a solid precipitate; and d) treating the solid precipitate with a second titanium compound in the presence of a second non-phthalate electron donor to form the solid catalyst component, where the process is free of carboxylic acids and anhydrides.

19 Claims, 7 Drawing Sheets

(56) References Cited

U.S. PATENT DOCUMENTS

| | | |
|---|---|---|
| 8,211,819 B2 | 7/2012 | Chang |
| 8,227,370 B2 | 7/2012 | Chang |
| 8,318,626 B2 | 11/2012 | Chang |
| 8,765,626 B2 | 7/2014 | Chang |
| 8,778,826 B2 | 7/2014 | Gonzalez et al. |
| 8,779,058 B2 | 7/2014 | Sheard et al. |
| 8,822,602 B2 | 9/2014 | Leskinen et al. |
| 8,841,390 B2 | 9/2014 | Leskinen et al. |
| 8,933,180 B2 | 1/2015 | Chang |
| 9,593,182 B2 | 3/2017 | Marin et al. |
| 9,637,575 B2 | 5/2017 | Nguyen et al. |
| 9,663,595 B2 | 5/2017 | Nguyen et al. |
| 9,663,647 B2 | 5/2017 | Van Egmond et al. |
| 9,714,302 B2 | 7/2017 | Umezawa-Vizzini et al. |
| 9,738,736 B2 | 8/2017 | Marin et al. |
| 9,751,960 B2 | 9/2017 | Li et al. |
| 9,890,274 B2 | 2/2018 | Wang et al. |
| 10,059,784 B2 | 8/2018 | Van Egmond |
| 10,208,145 B2 * | 2/2019 | Gao ............... C08F 110/06 |
| 10,208,146 B2 | 2/2019 | Wang et al. |
| 10,358,505 B2 | 7/2019 | Chen et al. |
| 10,526,427 B2 | 1/2020 | Fukuda et al. |
| 10,662,267 B2 | 5/2020 | Nguyen et al. |
| 10,759,931 B2 | 9/2020 | Kniesel et al. |
| 11,421,056 B2 * | 8/2022 | Marin ............... B01J 21/10 |
| 11,634,520 B2 * | 4/2023 | Marin ............ C08F 4/6586 526/100 |
| 11,891,460 B2 * | 2/2024 | Marin ............... C08F 110/06 |
| 2001/0008869 A1 | 7/2001 | Garoff et al. |
| 2001/0031840 A1 | 10/2001 | Kumamoto et al. |
| 2002/0169072 A1 | 11/2002 | Nakayama et al. |
| 2003/0236365 A1 | 12/2003 | Tian et al. |
| 2005/0038208 A1 | 2/2005 | Dahn et al. |
| 2005/0054792 A1 | 3/2005 | Kilty et al. |
| 2007/0032375 A1 | 2/2007 | Campbell et al. |
| 2009/0171044 A1 | 7/2009 | Spencer |
| 2010/0173769 A1 | 7/2010 | Gonzalez et al. |
| 2010/0240836 A1 | 9/2010 | Denifl et al. |
| 2010/0249330 A1 | 9/2010 | Massari et al. |
| 2012/0004378 A1 | 1/2012 | Hosaka |
| 2012/0035338 A1 * | 2/2012 | Tan ............... C08F 10/00 502/107 |
| 2012/0157645 A1 | 6/2012 | Chen et al. |
| 2012/0277090 A1 | 11/2012 | Spencer et al. |
| 2013/0035227 A1 | 2/2013 | Chen et al. |
| 2013/0102744 A1 | 4/2013 | Fushimi et al. |
| 2013/0225398 A1 | 8/2013 | Chen et al. |
| 2013/0261273 A1 | 10/2013 | Chen et al. |
| 2013/0296510 A1 * | 11/2013 | Guo ............... C08F 10/06 502/158 |
| 2015/0099842 A1 | 4/2015 | Gahleitner et al. |
| 2016/0102156 A1 | 4/2016 | Umezawa-Vizzini et al. |
| 2016/0289436 A1 | 10/2016 | Van Egmond et al. |
| 2016/0297906 A1 | 10/2016 | Van Egmond |
| 2017/0009068 A1 | 1/2017 | Kahlen et al. |
| 2017/0096503 A1 | 4/2017 | Marin et al. |
| 2017/0313865 A1 | 11/2017 | Wang et al. |

FOREIGN PATENT DOCUMENTS

| | | |
|---|---|---|
| CN | 101993506 A | 3/2011 |
| CN | 104558263 A | 4/2015 |
| CN | 104558275 A | 4/2015 |
| CN | 105622789 A | 6/2016 |
| EP | 1 508 559 A1 | 2/2005 |
| JP | 2004-051981 A | 2/2004 |
| JP | 2013-213074 A | 10/2013 |
| JP | 2014-512451 A | 5/2014 |
| JP | 2016-538396 A | 12/2016 |
| KR | 2010-0114888 A | 10/2010 |
| RU | 2265614 C2 | 12/2005 |
| RU | 2502746 C2 | 12/2013 |
| RU | 2527036 C2 | 8/2014 |
| RU | 2528384 C2 | 9/2014 |
| RU | 2532543 C2 | 11/2014 |
| WO | WO-2012/062734 A1 | 5/2012 |
| WO | WO-2012/088028 A1 | 6/2012 |
| WO | WO-2015/055137 A1 | 4/2015 |
| WO | WO-2015/185490 A1 | 12/2015 |

OTHER PUBLICATIONS

CN Search Report dated Aug. 4, 2022 for CN patent application No. 201880081336.1 (4 pages).
Foreign Action other than Search Report on JP patent application No. 2020-544377 dated Sep. 1, 2022.
Foreign Action other than Search Report on RU patent application No. 2020119397 dated Aug. 17, 2022.
Technical Examination Report on BR patent application No. BR112020009437-4 dated Mar. 20, 2023 (19 pages).
Communication pursuant to Rule 164(1) EPC re Partial Supplementary European Search Report on EP 18875540.9 dated Oct. 20, 2021 (7 pages).
Extended European Search Report on EP Application 18876554.9 dated Oct. 28, 2021 (4 pages).
Extended European Search Report on EP Application No. 18875540.9 dated Apr. 28, 2022 (16 pages).
First Examination Report on IN Application 202017019820 dated Nov. 16, 2021 (5 pages) (English translation included).
First Examination Report on IN Application No. 202017019815 dated Nov. 26, 2021 (8 pages) (English translation included).
Forte, et al., "Highly active magnesium chloride supported Ziegler-Natta catalysts with controlled morphology", European Polymer Journal, Pergamon Press Ltd Oxtord, GB, vol. 32, No. 2, Feb. 1, 1996 (Feb. 1, 1996), pp. 223-231.
International Preliminary Report on Patentability on PCT/US2018/057980 dated May 19, 2020 (7 pages).
International Preliminary Report on Patentability on PCT/US2018/059311 dated May 19, 2020 (7 pages).
International Preliminary Report on Patentability on PCT/US2018/060768 dated May 19, 2020 (6 pages).
International Search Report and Written Opinion on PCT/US2018/057980 dated Jan. 15, 2019 (9 pages).
International Search Report and Written Opinion on PCT/US2018/059311 dated Jan. 16, 2019 (9 pages).
International Search Report and Written Opinion on PCT/US2018/060768 dated Mar. 18, 2019 (9 pages).
Office Action and Search Report from RU 2020119468 dated Feb. 10, 2022 (English translation included, 31 pages).
Office Action and Search Report on RU Application No. 2020119397 dated Mar. 23, 2022 (English translation included, 29 pages).
Office Action and Search Report on TW Application No. 107139803 dated Apr. 26, 2022 (English translation included, 17 pages).
Partial Supplementary European Search Report on EP 18875540.9 dated Oct. 20, 2021 (6 pages).

* cited by examiner

PROCESS FOR PREPARING SOLID CATALYST COMPONENTS FOR OLEFIN POLYMERIZATION

RELATED APPLICATIONS

The present application is a continuation of U.S. patent application Ser. No. 16/762,331, filed on May 7, 2020, now U.S. Pat. No. 11,634,520, which is a U.S. national stage of PCT/US2018/059311, filed on Nov. 6, 2018, which in turn claims priority to U.S. Provisional Patent application Ser. No. 62/585,137, filed on Nov. 13, 2017, all of which are incorporated herein by reference in their entirety for all purposes.

TECHNICAL FIELD

The present disclosure relates to a process for the production of polymerization catalyst components, catalyst systems formed from the catalyst components, and methods of making the catalyst systems and olefin polymers and copolymers using the catalyst systems as described. More particularly, it relates to where the catalyst components are phthalate free.

BACKGROUND

Polyolefins are a class of polymers derived from simple olefins. Known methods of making polyolefins involve the use of Ziegler-Natta polymerization catalysts. These catalysts polymerize olefin monomers using a transition metal halide to provide a polymer with various types of stereochemical configurations.

One type of Ziegler-Natta catalyst system comprises a solid catalyst component, constituted by a magnesium halide on which are supported a titanium compound and an internal electron donor compound. In order to maintain high selectivity for an isotactic polymer product, internal electron donor compounds must be added during catalyst synthesis. The internal donor can be of various types. Conventionally, when a higher crystallinity of the polymer is required, an external donor compound is also added during the polymerization reaction.

During the past 30 years, numerous supported Ziegler-Natta catalysts have been developed which afford a much higher activity in olefin polymerization reactions and much higher content of crystalline isotactic fractions in the polymers they produce. With the development of internal and external electron donor compounds, polyolefin catalyst systems are continuously renovated.

Catalyst morphology control is an important aspect of industrial polyolefin plant operation. Catalyst morphology characteristics include particle size and particle size distribution, particle shape, and surface texture.

Catalyst morphology characteristics influence polymer powder properties such as the bulk density, flowability, degassing and particle adhesion. Such properties greatly influence plant operation efficiency. For example, unsuitable catalyst morphology may cause failure in polymer morphology control, which can lead to serious trouble in plant operation, such as fouling or sheeting.

Because of these reasons, $MgCl_2$ supported catalysts with good morphology control (required particle size and shape, narrow particle size distribution, high bulk density and low adhesion) are desired.

The general production scheme for $MgCl_2$ supported catalysts includes a process to make $MgCl_2$ support, impregnation of $TiCl_4$ and Lewis base, and internal donor to the $MgCl_2$ surface. One of the methods of $MgCl_2$ supported catalyst preparation is the reaction of $Mg(OR)Cl$ or $Mg(OR)_2$ with excess $TiCl_4$ diluted in aromatic or halogenated solvents. In such a case, $MgCl_2$ support is formed from the reaction between the magnesium compound and $TiCl_4$ and the internal donor is added to the process during or after the precipitation of the solid support.

In another method, the alkoxy magnesium complex reacts first with electron donor precursor and then with $TiCl_4$. In this process, the electron donor precursor is converted to the desired internal donor during the formation of $MgCl_2$.

In another method, the solid $MgCl_2$ is used to prepare the $MgCl_2$ catalyst. The solid $MgCl_2$ is dissolved in suitable solvents such as alcohol. The solution is then treated with $TiCl_4$ to precipitate the supported $MgCl_2$ catalyst. For example, $MgCl_2$ can be dissolved in hot ethanol and precipitated in cooled hexane in presence of tetraethylorthosilicate (TEOS).

U.S. Pat. Nos. 6,376,417; 4,784,983; and 4,861,847 describe a catalyst system for use in olefinic polymerization prepared by dissolving a halide of magnesium in a solvent system consisting of an organic compound, an organic phosphorus compound and an inert diluent to form a homogenous solution; mixing the homogenous solution with a halide of titanium to form a mixture; precipitating a solid from the mixture in the presence of an auxiliary precipitating agent; treating the solid with a polycarboxylic ester to load the ester on the solid; and treating the ester loaded with the halide of titanium and the inert diluent. U.S. Pat. No. 9,714,302 requires the use of carboxylic acids, anhydrides, and phthalates to be used in preparing the solid catalysts. A need remains in the art, however, for improved Ziegler-Natta catalyst that have higher and/or longer activity during polymerization processes. A need also exists for a catalyst capable of producing polymer particles with improved morphology.

SUMMARY

In one aspect, a process of preparing a solid catalyst component for the production of a polyolefin, such as polypropylene is provided, the process comprising:
  a) dissolving a halide-containing magnesium compound in a mixture, the mixture comprising an epoxy compound, an organic phosphorus compound, and a hydrocarbon solvent to form a homogenous solution;
  b) treating the homogenous solution with a first titanium compound in the presence of with an organosilicon compound, to form a solid precipitate;
  c) treating the solid precipitate with a second titanium compound in the presence of a non-phthalate electron donor to form the solid catalyst component;
wherein:
the process is free of carboxylic acids and anhydrides;
the first titanium compound and the second titanium compound are independently represented by:

$$Ti(OR)_g X_{4-g};$$

each R is independently a C1-C4 alkyl;
X is Br, Cl, or I; and
g is 0, 1, 2, or 3 and
the organosilicon compound contains O—Si—O or Si—O—Si groups or both of them.

The epoxy compound may include a glycidyl-containing compound represented by Formula:

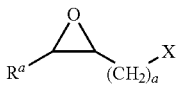

wherein:
a is 1,2,3,4, or 5;
X is alkyl, F, Cl, Br, I; and
$R^a$ is H, alkyl, aryl, or cyclyl.

In any of the above embodiments, X is methyl, ethyl, F, Cl, Br, or I. In yet other embodiments, the epoxy compound is selected from the group consisting of: ethylene oxide; propylene oxide; 1,2-epoxybutane; 2,3-epoxybutane; 1,2-epoxyhexane; 1,2-epoxyoctane; 1,2-epoxydecane; 1,2-epoxydodecane; 1,2-epoxytetradecane; 1,2-epoxyhexadecane; 1,2-epoxyoctadecane; 7,8-epoxy-2-methyloctadecane; 2-vinyl oxirane; 2-methyl-2-vinyl oxirane; 1,2-epoxy-5-hexene; 1,2-epoxy-7-octene; 1-phenyl-2,3-epoxypropane; 1-(1-naphthyl)-2,3-epoxypropane; 1-cyclohexyl-3,4-epoxybutane; 1,3-butadiene dioxide; 1,2,7,8-diepoxyoctane; cyclopentene oxide; cyclooctene oxide; α-pinene oxide; 2,3-epoxynorbornane; limonene oxide; cyclodecane epoxide; 2,3,5,6-diepoxynorbornane; styrene oxide; 3-methylstyrene oxide; 1,2-epoxybutylbenzene; 1,2-epoxyoctylbenzene; stilbene oxide; 3-vinylstyrene oxide; 1-(1-methyl-1,2-epoxyethyl)-3-(1-methylvinyl benzene); 1,4-bis(1,2-epoxypropyl)benzene; 1,3-bis(1,2-epoxy-1-methylethyl)benzene; 1,4-bis(1,2-epoxy-1-methylethyl)benzene; epifluorohydrin; epichlorohydrin; epibromohydrin; hexafluoropropylene oxide; 1,2-epoxy-4-fluorobutane; 1-(2,3-epoxypropyl)-4-fluorobenzene; 1-(3,4-epoxybutyl)-2-fluorobenzene; 1-(2,3-epoxypropyl)-4-chlorobenzene; 1-(3,4-epoxybutyl)-3-chlorobenzene; 4-fluoro-1,2-cyclohexene oxide; 6-chloro-2,3-epoxybicyclo[2.2.1]heptane; 4-fluorostyrene oxide; 1-(1,2-epoxypropyl)-3-trifluorobenzene; 3-acetyl-1,2-epoxypropane; 4-benzoyl-1,2-epoxybutane; 4-(4-benzoyl)phenyl-1,2-epoxybutane; 4,4'-bis(3,4-epoxybutyl) benzophenone; 3,4-epoxy-1-cyclohexanone; 2,3-epoxy-5-oxobicyclo[2.2.1]heptane; 3-acetylstyrene oxide; 4-(1,2-epoxypropyl)benzophenone; glycidyl methyl ether; butyl glycidyl ether; 2-ethylhexyl glycidyl ether; allyl glycidyl ether; ethyl 3,4-epoxybutyl ether; glycidyl phenyl ether; glycidyl 4-tert-butylphenyl ether, glycidyl 4-chlorophenyl ether; glycidyl 4-methoxyphenyl ether; glycidyl 2-phenylphenyl ether; glycidyl 1-naphthyl ether; glycidyl 2-phenylphenyl ether, glycidyl 1-naphthyl ether, glycidyl 4-indolyl ether; glycidyl N-methyl-α-quinolon-4-yl ether; ethylene glycol diglycidyl ether, 1,4-butanediol diglycidyl ether, 1,2-diglycidyloxybenzene; 2,2-bis(4-glycidyloxyphenyl)propane; tris(4-glycidyloxyphenyl)methane; poly(oxypropylene)triol triglycidyl ether; a glycidic ether of phenol novolac; 1,2-epoxy-4-methoxycyclohexane; 2,3-epoxy-5,6-dimethoxybicyclo[2.2.1]heptane; 4-methoxystyrene oxide; 1-(1,2-epoxybutyl)-2-phenoxybenzene; glycidyl formate; glycidyl acetate; 2,3-epoxybutyl acetate; glycidyl butyrate; glycidyl benzoate; diglycidyl terephthalate; poly(glycidyl acrylate); poly(glycidyl methacrylate); a copolymer of glycidyl acrylate with another monomer; a copolymer of glycidyl methacrylate with another monomer; 1,2-epoxy-4-methoxycarbonylcyclohexane; 2,3-epoxy-5-butoxycarbonylbicyclo[2.2.1]heptane; ethyl 4-(1,2-epoxyethyl)benzoate; methyl 3-(1,2-epoxybutyl)benzoate; methyl 3-(1,2-epoxybutyl)-5-pheylbenzoate; N,N-glycidylmethylacetamide; N,N-ethylglycidylpropionamide; N,N-glycidylmethylbenzamide; N-(4,5-epoxypentyl)-N-methylbenzamide; N,N-diglycidylaniline; bis(4-diglycidylaminophenyl)methane; poly(N,N-glycidylmethylacrylamide); 1,2-epoxy-3-(diphenylcarbamoyl)cyclohexane; 2,3-epoxy-6-(dimethylcarbamoyl)bicycle[2.2.1]heptane; 2-(dimethylcarbamoyl)styrene oxide; 4-(1,2-epoxybutyl)-4'-(dimethylcarbamoyl)biphenyl; 4-cyano-1,2-epoxybutane; 1-(3-cyanophenyl)-2,3-epoxybutane; 2-cyanostyrene oxide; and 6-cyano-1-(1,2-epoxy-2-phenylethyl)naphthalene.

In any of the above embodiments, steps a) and b) may be performed in the presence of a di-($C_1$-$C_{12}$)-alkylether.

In the above embodiments, the process may also include addition of the organosilicon compound during, or after, the dissolution of Mg-compound in the organic solvent including epoxy organic compound in step a). Illustrative organosilicon compounds include, but are not limited to, a silane, a siloxane, or a polysiloxane. In some embodiments, the organosilicon compound may be represented as Formula (II):

$$R_nSi(OR')_{4-n} \qquad (II).$$

In Formula (II) each R may be H, alkyl, or aryl; each R' may be H, alkyl, aryl, or —$SiR_n'(OR')_{3-n}$, where n is 0, 1, 2, or 3.

In some embodiments, the organosilicon is a monomeric or polymeric compound. The organosilicon compound may contain —Si—O—Si— groups inside of one molecule or between others. Other illustrative examples of an organosilicon compound include polydialkylsiloxane and/or tetraalkoxysilane. Such compounds may be used individually or as a combination thereof. The organosilicon compound may be used with combination of aluminum alkoxides and the first internal donor. In some embodiments, polydimethylsiloxane and/or tetraethoxysilane may be used. The aluminum alkoxide referred to above may be of formula Al(OR')$_3$ where each R' is individually a hydrocarbon with up to 20 carbon atoms. This may include where each R' is individually methyl, ethyl, n-propyl, iso-propyl, n-butyl, sec-butyl, tert-butyl, n-pentyl, iso-pentyl, neo-pentyl, etc.

As described above, the process can occur in the presence of a non-phthalate electron donor. In one embodiment, the process can occur in the presence of a supportive donor. In one embodiment, the process occurs in the presence of a supportive donor (which may also be a first non-phthalate electron donor) and in the presence of a second non-phthalate electron donor.

The supportive donor or first non-phthalate donor may include a diether, succinate, oxygen-containing electron donors such as organic acid ester, polycarboxylic acid ester, polyhydroxy ester, heterocyclic polycarboxylic acid esters, inorganic acid ester, alicyclic polycarboxylic acid ester, and hydroxy-substituted carboxylic acid esters compounds having 2 to about 30 carbon atoms. For example, the first non-phthalate donor may include methyl formate; ethyl acetate; vinyl acetate; propyl acetate; octyl acetate; cyclohexyl acetate; ethyl propionate; methyl butyrate; ethyl valerate; ethyl stearate; methyl chloroacetate; ethyl dichloroacetate; methyl methacrylate; ethyl crotonate; dibutyl maleate; diethyl butylmalonate; diethyl dibutylmalonate; ethyl cyclohexanecarboxylate; diethyl 1,2-cyclohexanedicarboxylate; di-2-ethylhexyl 1,2-cyclohexanedicarboxylate; methyl benzoate; ethyl benzoate; propyl benzoate; butyl benzoate; octyl benzoate; cyclohexyl benzoate; phenyl benzoate; benzyl benzoate; methyl toluate; ethyl toluate; amyl toluate; ethyl ethylbenzoate; methyl anisate; ethyl anisate; ethyl ethoxybenzoate, γ-butyrolactone; δ-valerolactone; coumarine; phthalide; ethylene carbonate; ethyl silicate; butyl silicate; vinyltriethoxysilane; phenyltriethoxysilane; diphenyldiethoxysilane; diethyl 1,2-cyclohexanecarboxylate; diisobutyl 1,2-cyclohexanecarboxylate; diethyl tetrahydrophthalate and nadic acid; diethyl ester; diethyl naphthalenedicarboxylate; dibutyl naphthlenedicarboxylate; triethyl trimellitate and dibutyl trimellitate; 3,4-furanedicarboxylic acid esters; 1,2-diacetoxybenzene; 1-methyl-2,3-diacetoxybenzene; 2-methyl-2,3-diacetoxybenzene; 2,8-diacetoxynaphthalene; ethylene glycol dipivalate; butanediol pivalate; benzoylethyl salicylate; acetylisobutyl salicylate; acetylmethyl salicylate; diethyl adipate; diisobutyl adipate; diisopropyl sebacate; di-n-butyl sebacate; di-n-octyl sebacate; or di-2-ethylhexyl sebacate.

In any of the above embodiments, the supportive donor or first non-phthalate donor may be selected from the group consisting of methyl formate, butyl formate, ethyl acetate, vinyl acetate, propyl acetate, octyl acetate, cyclohexyl acetate, ethyl propionate, methyl butyrate, ethyl butyrate, isobutyl butyrate, ethyl valerate, ethyl stearate, methyl chloroacetate, ethyl dichloroacetate, ethyl acrylate, methyl methacrylate, ethyl crotonate, ethyl cyclohexanecarboxylate, methyl benzoate, ethyl benzoate, propyl benzoate, butyl benzoate, octyl benzoate, cyclohexyl benzoate, phenyl benzoate, benzyl benzoate, ethyl p-methoxybenzoate, methyl p-methyl benzoate, ethyl p-t-butylbenzoate, ethyl naphthoate, methyl toluate, ethyl toluate, amyl toluate, ethyl ethyl benzoate, methyl anisate, ethyl anisate, and ethyl ethoxybenzoate.

In any of the above embodiments, the second non-phthalate electron donor may include a compound different from the supportive donor and is a compound that is a diether, succinate, oxygen-containing electron donors such as organic acid ester, polycarboxylic acid ester, polyhydroxy ester, heterocyclic polycarboxylic acid esters, inorganic acid ester, alicyclic polycarboxylic acid ester, a hydroxy-substituted carboxylic acid esters compound having 2 to about 30 carbon atoms, or a compound having at least one ether group and at least one ketone group.

In many of the above embodiments, the second non-phthalate donor may be selected from the group consisting of linear or cyclic diethers, and non-phthalate aromatic diesters. For example, in one embodiment, the second electron donor may comprise an aryl ester. In one particular embodiment, the electron donor may comprise a substituted 1,2-phenylene dibenzoate. Various electron donors may include compounds represented by the following formulas:

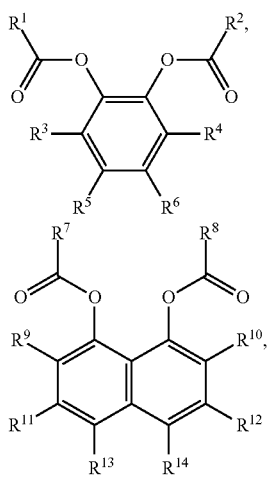

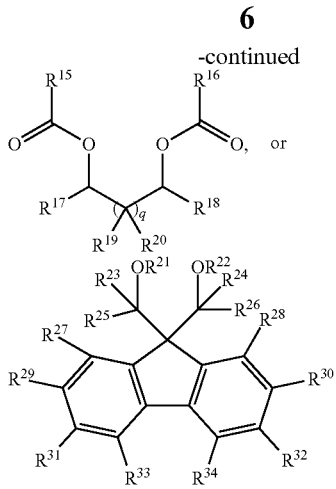

where each of $R^1$ through $R^{34}$ is independently H, F, Cl, Br, I, alkyl, cycloalkyl, cycloalkylalkyl, aryl, aralkyl, heterocyclyl, heterocyclylalkyl, heteroaryl, or heteroarylalkyl; and q is an integer from 0 to 12.

In any of the above embodiments, the treating the homogenous solution with the first titanium compound is conducted in the presence of an organic ester and a organosilicon compound; an organic ester and an aluminum alkoxide; or an organic ester, an organosilicon compound, and an aluminum alkoxide; to form the solid precipitate.

In any of the above embodiments, the hydrocarbon solvent comprises an aromatic solvent, a non-aromatic solvent, or a mixture of any two or more thereof.

In many of the above embodiments, the hydrocarbon solvent comprises a ($C_1$-$C_{20}$-alkyl)benzene, hexane, heptane, or a mixture of any two or more thereof. For example, the hydrocarbon solvent may include toluene, hexane, heptane, or a mixture of any two or more thereof.

In any of the above embodiments, step c) comprises the treating with the first titanium compound, the second titanium compound, or a mixture thereof is conducted at a temperature of from about −25° C. to about 150° C.

In any of the above embodiments, the halide-containing magnesium compound is selected from the group consisting of magnesium chloride, magnesium bromide, magnesium iodide, magnesium fluoride, and a mixture of any two or more thereof.

In any of the above embodiments, the organic phosphorus compound is represented by:

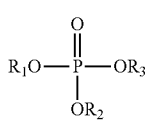

wherein $R_1$, $R_2$, and $R_3$ are each independently $C_1$-$C_{10}$ alkyl.

In the above embodiments, the di-($C_1$-$C_{12}$)alkylether may be selected from the group consisting of: dimethyl ether, diethyl ether, dipropyl ether, di-n-butyl ether, butyl propyl ether, diamyl ether, diisoamyl ether, dihexyl ether, and mixtures of any two or more thereof.

In any of the above embodiments, the organosilicon compound may be a siloxane or polysiloxane represented as Formula:

wherein:
each R is H, alkyl, or aryl;
each R' is H, alkyl, aryl, or a $SiR_n(OR')_{3-n}$; and
n is 0, 1, 2, or 3.

The present disclosure is also directed to a solid catalyst component. The solid catalyst component, in one embodiment, comprises:
a magnesium compound including a halide-containing magnesium compound and a reaction product of a magnesium compound with an epoxy compound;
an organic phosphorus compound;
a titanium compound;
an organosilicon compound containing: Si—O, or O—Si—O groups;
an internal electron donor, the internal electron donor comprising an aryl diester, a 1,2-phenylene dibenzoate, a diether, a succinate, an organic acid ester, a polycarboxylic acid ester, a polyhydroxy ester, a heterocyclic polycarboxylic acid ester, an inorganic acid ester, an alicyclic polycarboxylic acid ester, a hydroxy-substituted carboxylic acid ester compound having 2 to 30 carbon atoms, or a compound having at least one ether group and at least one ketone group, or mixtures thereof;
wherein the solid catalyst component is free of side reaction products between a carboxylic acid or an anhydride thereof and a magnesium compound or a titanium compound, and
wherein the solid catalyst component has a particle size from about 5 microns to about 70 microns (on a 50% by volume basis).

In another aspect, a catalyst system for use in olefinic polymerization is provided, the catalyst system comprising the solid catalyst component produced by the process of any of the above processes, an organoaluminum compound, and optionally, an organosilicon compound.

In any of the above catalyst system embodiments the organoaluminum compound may be an alkyl-aluminum compound. For example it may be a trialkyl aluminum compound such as triethylaluminum, triisobutylaluminum, or tri-n-octylaluminum.

In another aspect, a process is provided for polymerizing or copolymerizing a polypropylene monomer, the process may include contacting an olefinic monomer, or a mixture of olefinic monomers with any of the above catalyst systems and a homopolymer of the olefinic monomer or a co-polymer of a mixture of olefinic monomers.

A process for polymerizing or copolymerizing an olefinic monomer, the process comprising contacting polypropylene monomer, or a mixture of polypropylene with at least one other olefinic monomer, with the catalyst system as described herein to form polypropylene or a co-polymer of polypropylene and the olefinic monomers.

DETAILED DESCRIPTION

Figure 1:
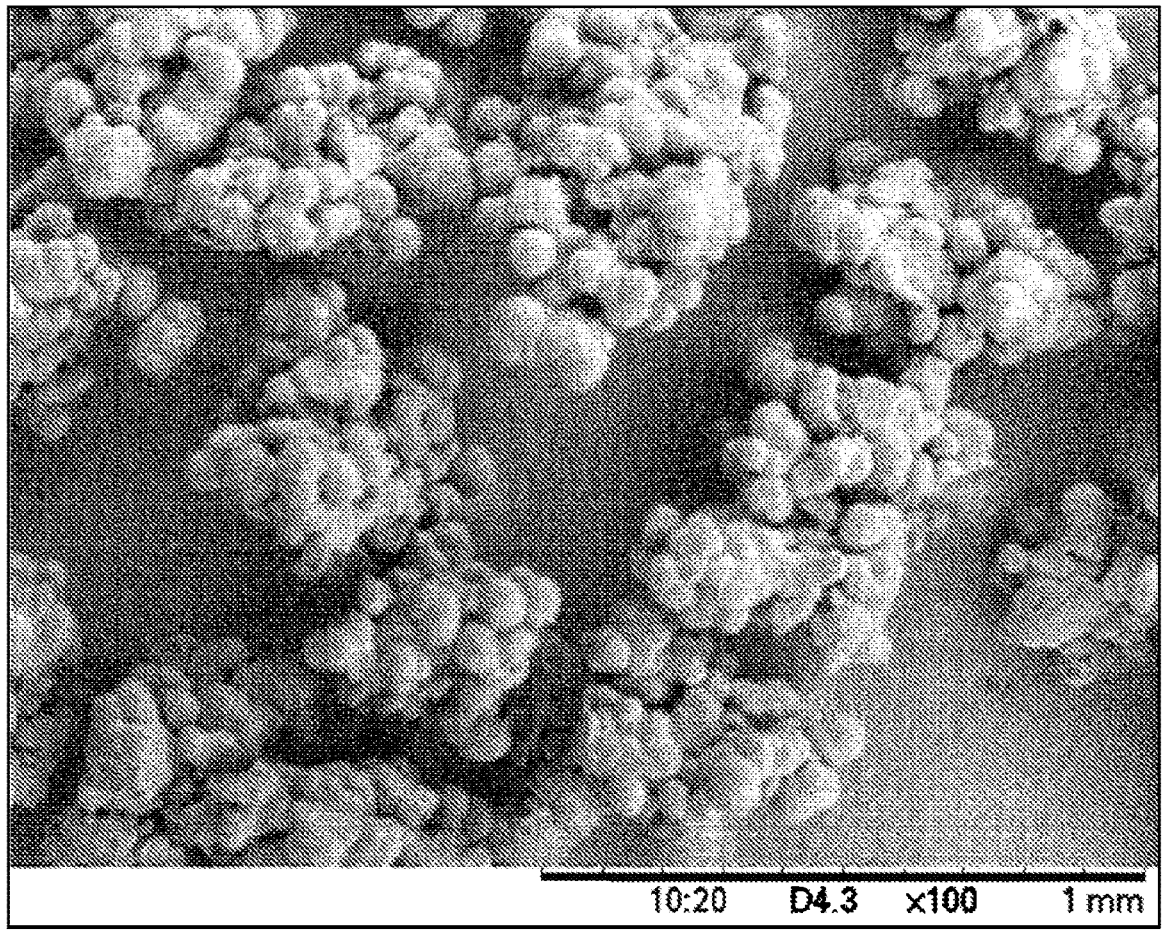
FIG. 1 shows a microscopic view of the polymer produced with the catalyst component of Example 5 (Comparative).

Before describing several exemplary embodiments, it is to be understood that the invention is not limited to the details of construction or process steps set forth in the following description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment. Thus, the appearances of the phrases such as "in one or more embodiments," "in certain embodiments," "in one embodiment" or "in an embodiment" in various places throughout this specification are not necessarily referring to the same embodiment. Furthermore, the particular features, structures, materials, or characteristics may be combined in any suitable manner in one or more embodiments.

Although reference herein is to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

Described herein are Ziegler-Natta catalyst systems and supports for Ziegler-Natta catalysts and methods of making the same. One aspect of the catalyst systems is a solid catalyst component containing a halide-containing magnesium compound and titanium compound for polymerizing an olefin, where the solid catalyst component has substantially spherical or spheroidal shape. The solid catalyst component can be used to form a competent Ziegler-Natta catalyst in combination with one or more external and/or internal electron donors and an organoaluminum compound.

As used throughout this disclosure, the term "solid catalyst component" refers to a pre-catalyst containing a halide-containing magnesium compound and titanium compound, and optionally one or more internal electron donors that are useful for forming a competent Ziegler-Natta catalyst system upon combination with a main group metal alkyl.

In a typical manner of employing the Ziegler-Natta catalyst system, a solid catalyst component, an electron donor, and an organoaluminum compound (a main group metal alkyl) form a slurry catalyst system, which can contain any suitable liquid such as an inert hydrocarbon medium. Examples of inert hydrocarbon media include aliphatic hydrocarbons such as propane, butane, pentane, hexane, heptane, octane, decane, dodecane and kerosene; alicyclic hydrocarbons such as cyclopentane, cyclohexane and methylcyclopentane; aromatic hydrocarbons such as benzene, toluene and xylene; halogenated hydrocarbons such as ethylene chloride and chlorobenzene; and mixtures thereof. The slurry medium can be hexane, heptane or mineral oil. The slurry medium can be different from the diluent used in forming the mixture from which the solid catalyst component is precipitated.

The herein described solid catalyst supports can be utilized in any suitable Ziegler-Natta polymerization catalyst system. Ziegler-Natta catalyst systems include a reagent or combination of reagents that are functional to catalyze the polymerization of 1-alkenes (α-olefins) to form polymers, typically with high isotacticity, when pro-chiral 1-alkenes are polymerized. The term "Ziegler-Natta catalyst" refers to any composition having a transition metal and a main group metal alkyl component capable of supporting catalysis of 1-alkene polymerization. The transition metal component is typically a Group IV metal such as titanium, or vanadium, the main group metal alkyl is typically an organoaluminum compound having a carbon-Al bond, and the electron donor can be any of numerous compounds including aromatic esters, alkoxysilanes, amines and ketones can be used as external donors added to the transition metal component and the main group metal alkyl component or an appropriate internal donor added to the transition metal component and the main group metal alkyl component during synthesis of those components.

Described herein are methods of making a solid catalyst component for use in a Ziegler-Natta catalyst, and the methods and catalysts are free of carboxylic acid or anhydrides. By being free of the carboxylic acids and/or anhydrides, the catalysts provide high activity due to absence of side products of the reaction between the carboxylic acid and/or anhydride with the magnesium compounds and $TiCl_4$, that may otherwise result in the deactivation of active centers in polymerization process.

The catalyst/support morphology is a key factor to consider in any commercial polymer production process. To control the catalyst/support morphology variable techniques and processes are used. One such technique is to use a surfactant during the support formation. Surfactants are compounds that lower the surface tension (or interfacial tension) between two liquids or between a liquid and a solid. Surfactants are usually polar organic compounds, and they can be removed from the solid catalyst or can partly stay on the catalyst surface. Surfactants may also act as a supportive internal donor interacting with the main internal donor or act as a negative component deactivating catalytic active center during the polymerization process.

In a first aspect, a process is provided for preparing a solid catalyst component for the production of a polyolefin, such as a polypropylene. The processes include dissolving a halide-containing magnesium compound in a mixture, where the mixture includes epoxy compound, an organic phosphorus compound, and a first hydrocarbon solvent to form a homogenous solution. The homogenous solution is then treated with a first titanium compound in the presence of an organosilicon compound and optionally with a non-phthalate electron donor and/or supportive donor, and, to form a solid precipitate. The solid precipitate is then treated with a second titanium compound in the presence of a non-phthalate electron donor to form the solid catalyst component. The process is to be conducted free of carboxylic acids and anhydrides. Additionally, the dissolving and treating of the homogeneous solution may be performed sequentially or simultaneously. Finally, the first and second titanium compounds are, independently, represented as:

$$Ti(OR)_gX_{4-g}$$

where each R is independently a $C_1$-$C_4$ alkyl; X is Br, Cl, or I; and g is 0, 1, 2, 3, or 4.

The halide-containing magnesium compound, epoxy compound, and organic phosphorus compound are reacted in the presence of a hydrocarbon solvent. The hydrocarbon solvent can include aromatic or non-aromatic solvents or combinations thereof. In certain embodiments, the aromatic hydrocarbon solvent is selected from toluene and C2-C20 alkylbenzene. In certain embodiments, the nonaromatic hydrocarbon solvent is selected from hexane and heptane. In an embodiment, the hydrocarbon solvent is a mixture of toluene and hexane. In another embodiment, the hydrocarbon solvent is a mixture of ethylbenzene and heptane. In certain embodiments, a ratio of the non-aromatic solvent to the aromatic solvent is from 10:90 to 90:10 wt % or 30:70 to 70:30 wt % or 40:60 to 65:35 wt % or 50:50 to 45:55 wt %.

In a particular embodiment, the halide-containing magnesium compound, epoxy compound, and organic phosphorus compound are reacted in the presence of an organic solvent at a first temperature from about 25 to about 100° C. to form a homogenous solution. In another embodiment, the first temperature is from about 40 to about 90° C. or from about 50 to about 70° C. In a certain embodiment, the molar ratio of the magnesium compound to alkylepoxide is from about 0.1:2 to about 2:0.1 or about 1:0.25 to about 1:4 or about 1:0.9 to about 1:2.2. In a certain embodiment, the molar ratio of the magnesium compound to the Lewis base is from about 1:0.1 to about 1:4 or 0.5:1 to 2.0:1 or 1:0.7 to 1:1. Without wishing to be bound by any theory, it is believed that a halogen atom is transferred from the magnesium compound to the epoxy compound to open the epoxide ring and form an alkoxide magnesium species having a bond between the magnesium atom and the oxygen atom of the newly formed alkoxide group. During this process the organic phosphorus compound coordinates to Mg atom of halide-containing magnesium compound and increases the solubility of the magnesium-containing species present.

The process for preparing the solid catalyst component may also include addition of an organosilicon compound during, or after, the dissolution of the magnesium compound (Mg-compound) in the organic solvent, along with the epoxy compound. The organosilicon compound may be a silane, a siloxane, or a polysiloxane. The organosilicon compound, in some embodiments, may be represented as Formula (II):

$$R_nSi(OR')_{4-n} \tag{II}$$

In Formula (II) each R may be H, alkyl, or aryl; each R' may be H, alkyl, aryl, or —$SiR_n(OR')_{3-n}$, where n is 0, 1, 2, or 3.

In some embodiments, the organosilicon is a monomeric or polymeric compound. The organosilicon compound may contain —Si—O—Si— groups inside of one molecule or between others. Other illustrative examples of an organosilicon compound include polydialkylsiloxane and/or tetraalkoxysilane. Such compounds may be used individually or as a combination thereof. The organosilicon compound may be used with combination of aluminum alkoxides and the first internal donor. In some embodiments, polydimethylsiloxane and/or tetraethoxysilane may be used.

The aluminum alkoxide referred to above may be of formula $Al(OR')_3$ where each R' is individually a hydrocarbon with up to 20 carbon atoms. This may include where each R' is individually methyl, ethyl, n-propyl, iso-propyl, n-butyl, sec-butyl, tert-butyl, n-pentyl, iso-pentyl, neo-pentyl, etc. It is believed that the organosilicon compound reacts with the aluminum oxide during the catalyst component preparation, thereby forming compounds containing Al—

O—Si—O linkages. Therefore, these compounds can be prepared before the catalyst component synthesis and added directly to the process.

The organosilicon compound helps to precipitate the solid catalyst component from the solution. It is believed that the Si—O groups from the organosilicon compound coordinate to Mg atoms of the Mg-compound during the precipitation of solid catalyst component, thereby leading to a desired catalyst component morphology. This type of coordination is usually weak. Therefore, during the treatment of the solid catalyst component with the second Ti-compound and the second non-phthalate internal donor, they displace the organosilicon compound from the Mg compound, providing the high activity catalyst component.

It is known that the precipitation of the solid catalyst component using Mg compounds in an epoxy medium containing anhydrides or organic acids result in the certain side products containing derivatives formed by interaction of epoxy compounds with anhydrides or organic acids. These derivatives contain carbonyl groups coordinated strongly to Mg— atom and can be present on the final catalyst component, and lead to deactivation the catalyst active centers. The present catalyst systems, which are free of organic acids and/or anhydrides, address these deficiencies of the earlier systems.

The halide-containing magnesium compound in the homogenous solution is treated with a titanium halide compound to form a solid precipitate. The solution can be raised to a second temperature greater than the first temperature and a surface modifier can be added to control phase morphology. Also, when treating with a titanium halide compound, a non-phthalate electron donor is added. The first electron donor changes the viscosity and polarity of the solution that effects on the morphology precipitated particles, in particular, particle size, particle shape and particle density.

As noted above, the process is carried out in the presence of non-phthalate donors. In one embodiment, a supportive donor is used that may also be referred to as the first non-phthalate donor. The supportive donor or first non-phthalate donor may be a diether, succinate, diester, oxygen-containing electron donor such as an organic ester, polyester, polyhydroxy ester, heterocyclic polyester, inorganic esters, alicyclic polyester, and hydroxy-substituted esters having 2 to about 30 carbon atoms.

Illustrative first non-phthalate donors or supportive donors include methyl formate; ethyl acetate; vinyl acetate; propyl acetate; octyl acetate; cyclohexyl acetate; ethyl propionate; methyl butyrate; ethyl valerate; ethyl stearate; methyl chloroacetate; ethyl dichloroacetate; methyl methacrylate; ethyl crotonate; dibutyl maleate; diethyl butylmalonate; diethyl dibutylmalonate; ethyl cyclohexanecarboxylate; diethyl 1,2-cyclohexanedicarboxylate; di-2-ethylhexyl 1,2-cyclohexanedicarboxylate; methyl benzoate; ethyl benzoate; propyl benzoate; butyl benzoate; octyl benzoate; cyclohexyl benzoate; phenyl benzoate; benzyl benzoate; methyl toluate; ethyl toluate; amyl toluate; ethyl ethylbenzoate; methyl anisate; ethyl anisate; ethyl ethoxybenzoate, γ-butyrolactone; δ-valerolactone; coumarine; phthalide; ethylene carbonate; ethyl silicate; butyl silicate; vinyltriethoxysilane; phenyltriethoxysilane; diphenyldiethoxysilane; diethyl 1,2-cyclohexanecarboxylate; diisobutyl 1,2-cyclohexanecarboxylate; diethyl tetrahydrophthalate and nadic acid; diethyl ester; diethyl naphthalenedicarboxylate; dibutyl naphthlenedicarboxylate; triethyl trimellitate and dibutyl trimellitate; 3,4-furanedicarboxylic acid esters; 1,2-diacetoxybenzene; 1-methyl-2,3-diacetoxybenzene; 2-methyl-2,3-diacetoxybenzene; 2,8-diacetoxynaphthalene; ethylene glycol dipivalate; butanediol pivalate; benzoylethyl salicylate; acetylisobutyl salicylate; acetylmethyl salicylate; diethyl adipate; diisobutyl adipate; diisopropyl sebacate; di-n-butyl sebacate; di-n-octyl sebacate; or di-2-ethylhexyl sebacate. In some embodiments, the first non-phthalate donor is methyl formate, butyl formate, ethyl acetate, vinyl acetate, propyl acetate, octyl acetate, cyclohexyl acetate, ethyl propionate, methyl butyrate, ethyl butyrate, isobutyl butyrate, ethyl valerate, ethyl stearate, methyl chloroacetate, ethyl dichloroacetate, ethyl acrylate, methyl methacrylate, ethyl crotonate, ethyl cyclohexanecarboxylate, methyl benzoate, ethyl benzoate, propyl benzoate, butyl benzoate, octyl benzoate, cyclohexyl benzoate, phenyl benzoate, benzyl benzoate, ethyl p-methoxybenzoate, methyl p-methyl benzoate, ethyl p-t-butyl benzoate, ethyl naphthoate, methyl toluate, ethyl toluate, amyl toluate, ethyl ethyl benzoate, methyl anisate, ethyl anisate, or ethyl ethoxybenzoate.

The combination of different supportive donors or first internal donors and solvents can be used to produce a catalyst component with different morphology: i.e. granular and/or spherical. In particular, a catalyst component with granular support may be produced using mono-ester as a first internal donor with an aromatic or hydrocarbon solvent, while spherical type catalyst components may be produced using two or three different internal donors (e.g. mono-ester, dialkyl ether and acrylates) in a mixture of two solvents (aromatic and hydrocarbons).

In one embodiment, a supportive donor or first internal electron donor is used in conjunction with a second non-phthalate electron donor. Second non-phthalate electron donors may include compounds that are different from the first non-phthalate electron donor and is a compound that is a diether, succinate, oxygen-containing electron donors such as organic ester, polyester, polyhydroxy ester, heterocyclic polyester, inorganic esters, alicyclic polyester, and hydroxy-substituted esters having 2 to about 30 carbon atoms, or a compounding having at least one ether group and at least one ketone group. In some embodiments, the second non-phthalate donor is selected from the group consisting of linear of cyclic diethers, and non-phthalate aromatic diesters. In another embodiment, the second internal electron donor may be a dibenzoate, a dialkylate, and/or diarylate.

Additional illustrative second non-phthalate electron donors may include, alone or in combination with any of the above, compounds represented by the following formulas:

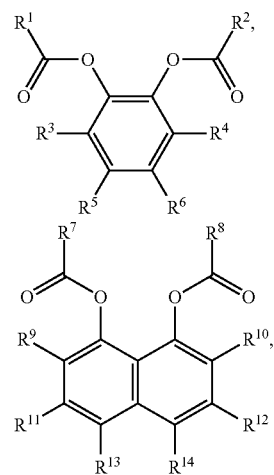

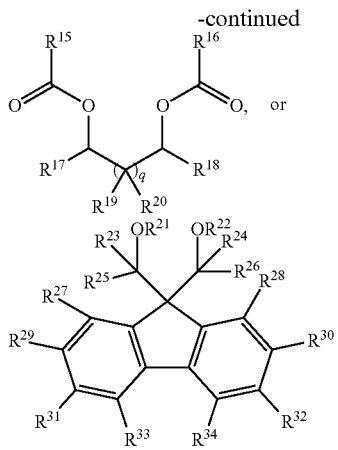

where each of $R^1$ through $R^{34}$ is independently H, F, Cl, Br, I, $OR^{33}$, alkyl, cycloalkyl, cycloalkylalkyl, aryl, aralkyl, heterocyclyl, heterocyclylalkyl, heteroaryl, or heteroarylalkyl; q is an integer from 0 to 12, wherein $R^{33}$ is a alkyl or heteroalkyl. Other non-phthalate donors may also include those as listed as internal electron donors in U.S. Pat. No. 9,045,570, incorporated by reference herein.

Examples of the halide-containing magnesium compound include magnesium chloride, magnesium bromide, magnesium iodide, and magnesium fluoride. In one embodiment, the halide-containing magnesium compound is magnesium chloride.

Illustrative the epoxy compounds include, but are not limited to, glycidyl-containing compounds of Formula:

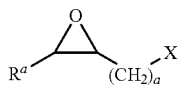

wherein "a" is from 1, 2, 3, 4, or 5, X is F, Cl, Br, I, or methyl, and $R^a$ is H, alkyl, aryl, or cyclyl. In one embodiment, the alkylepoxide is epichlorohydrin. In some embodiments, the epoxy compound is a haloalkylepoxide or a nonhaloalkylepoxide.

According to some embodiments, the epoxy compound is selected from the group consisting of ethylene oxide; propylene oxide; 1,2-epoxybutane; 2,3-epoxybutane; 1,2-epoxyhexane; 1,2-epoxyoctane; 1,2-epoxydecane; 1,2-epoxydodecane; 1,2-epoxytetradecane; 1,2-epoxyhexadecane; 1,2-epoxyoctadecane; 7,8-epoxy-2-methyloctadecane; 2-vinyl oxirane; 2-methyl-2-vinyl oxirane; 1,2-epoxy-5-hexene; 1,2-epoxy-7-octene; 1-phenyl-2,3-epoxypropane; 1-(1-naphthyl)-2,3-epoxypropane; 1-cyclohexyl-3,4-epoxybutane; 1,3-butadiene dioxide; 1,2,7,8-diepoxyoctane; cyclopentene oxide; cyclooctene oxide; α-pinene oxide; 2,3-epoxynorbornane; limonene oxide; cyclodecane epoxide; 2,3,5,6-diepoxynorbornane; styrene oxide; 3-methylstyrene oxide; 1,2-epoxybutylbenzene; 1,2-epoxyoctylbenzene; stilbene oxide; 3-vinylstyrene oxide; 1-(1-methyl-1,2-epoxyethyl)-3-(1-methylvinyl benzene); 1,4-bis(1,2-epoxypropyl) benzene; 1,3-bis(1,2-epoxy-1-methylethyl)benzene; 1,4-bis (1,2-epoxy-1-methylethyl)benzene; epifluorohydrin; epichlorohydrin; epibromohydrin; hexafluoropropylene oxide; 1,2-epoxy-4-fluorobutane; 1-(2,3-epoxypropyl)-4-fluorobenzene; 1-(3,4-epoxybutyl)-2-fluorobenzene; 1-(2,3-epoxypropyl)-4-chlorobenzene; 1-(3,4-epoxybutyl)-3-chlorobenzene; 4-fluoro-1,2-cyclohexene oxide; 6-chloro-2,3-epoxybicyclo[2.2.1]heptane; 4-fluorostyrene oxide; 1-(1,2-epoxypropyl)-3-trifluorobenzene; 3-acetyl-1,2-epoxypropane; 4-benzoyl-1,2-epoxybutane; 4-(4-benzoyl) phenyl-1,2-epoxybutane; 4,4'-bis(3,4-epoxybutyl) benzophenone; 3,4-epoxy-1-cyclohexanone; 2,3-epoxy-5-oxobicyclo[2.2.1]heptane; 3-acetylstyrene oxide; 4-(1,2-epoxypropyl)benzophenone; glycidyl methyl ether; butyl glycidyl ether; 2-ethylhexyl glycidyl ether; allyl glycidyl ether; ethyl 3,4-epoxybutyl ether; glycidyl phenyl ether, glycidyl 4-tert-butylphenyl ether; glycidyl 4-chlorophenyl ether, glycidyl 4-methoxyphenyl ether; glycidyl 2-phenylphenyl ether; glycidyl 1-naphthyl ether; glycidyl 2-phenylphenyl ether; glycidyl 1-naphthyl ether; glycidyl 4-indolyl ether; glycidyl N-methyl-α-quinolon-4-yl ether; ethyleneglycol diglycidyl ether, 1,4-butanediol diglycidyl ether, 1,2-diglycidyloxybenzene; 2,2-bis(4-glycidyloxyphenyl)propane; tris(4-glycidyloxyphenyl)methane; poly(oxypropylene)triol triglycidyl ether; a glycidic ether of phenol novolac; 1,2-epoxy-4-methoxycyclohexane; 2,3-epoxy-5,6-dimethoxybicyclo[2.2.1]heptane; 4-methoxystyrene oxide; 1-(1,2-epoxybutyl)-2-phenoxybenzene; glycidyl formate; glycidyl acetate; 2,3-epoxybutyl acetate; glycidyl butyrate; glycidyl benzoate; diglycidyl terephthalate; poly(glycidyl acrylate); poly(glycidyl methacrylate); a copolymer of glycidyl acrylate with another monomer; a copolymer of glycidyl methacrylate with another monomer; 1,2-epoxy-4-methoxycarbonylcyclohexane; 2,3-epoxy-5-butoxycarbonylbicyclo[2.2.1]heptane; ethyl 4-(1,2-epoxyethyl)benzoate; methyl 3-(1,2-epoxybutyl)benzoate; methyl 3-(1,2-epoxybutyl)-5-pheylbenzoate; N,N-glycidylmethylacetamide; N,N-ethylglycidylpropionamide; N,N-glycidylmethylbenzamide; N-(4,5-epoxypentyl)-N-methylbenzamide; N,N-diglycylaniline; bis(4-diglycidylaminophenyl)methane; poly(N,N-glycidylmethylacrylamide); 1,2-epoxy-3-(diphenylcarbamoyl)cyclohexane; 2,3-epoxy-6-(dimethylcarbamoyl)bicycle[2.2.1]heptane; 2-(dimethylcarbamoyl)styrene oxide; 4-(1,2-epoxybutyl)-4'-(dimethylcarbamoyl)biphenyl; 4-cyano-1,2-epoxybutane; 1-(3-cyanophenyl)-2,3-epoxybutane; 2-cyanostyrene oxide; and 6-cyano-1-(1,2-epoxy-2-phenylethyl)naphthalene.

As an example of the organic phosphorus compound, phosphate acid esters such as trialkyl phosphate acid ester may be named. Such compounds may be represented by Formula:

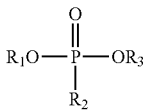

wherein $R_1$, $R_2$, and $R_3$ are each independently selected from the group consisting of methyl, ethyl, and linear or branched ($C_3$-$C_{10}$) alkyl groups. In one embodiment, the trialkyl phosphate acid ester is tributyl phosphate acid ester.

The halide-containing magnesium compound, epoxy compound, and organic phosphorus compound are contacted in the presence of a hydrocarbon solvent. The hydrocarbon solvent can include aromatic or non-aromatic solvents or combinations thereof. In certain embodiments, the aromatic hydrocarbon solvent is selected from toluene and $C_2$-$C_{20}$ alkylbenzene. In certain embodiments, the nonaromatic hydrocarbon solvent is selected from hexane and heptane. In an embodiment, the hydrocarbon solvent is a mixture of toluene and hexane. In another embodiment, the hydrocarbon solvent is a mixture of ethylbenzene and heptane. In certain embodiments, a ratio of the non-aromatic solvent to the aromatic solvent is from 10:90 to 90:10 wt % or 30:70 to 70:30 wt % or 40:60 to 65:35 wt % or 50:50 to 45:55 wt %.

In a particular embodiment, the halide-containing magnesium compound, epoxy compound, and organic phosphorus compound are contacted in the presence of an organic solvent at a first temperature from about 25 to about 100° C. to form a homogenous solution. In another embodiment, the first temperature is from about 40 to about 90° C. or from about 50 to about 70° C. In a certain embodiment, the molar ratio of the magnesium compound to alkylepoxide is from about 0.1:2 to about 2:0.1 or about 1:0.25 to about 1:4 or about 1:0.9 to about 1:2.2. In a certain embodiment, the molar ratio of the magnesium compound to the Lewis base is from about 1:0.1 to about 1:4 or 0.5:1 to 2.0:1 or 1:0.7 to 1:1. Without wishing to be bound by any theory, it is believed that a halogen atom is transferred from the magnesium compound to the epoxy compound to open the epoxide ring and form an alkoxide magnesium species having a bond between the magnesium atom and the oxygen atom of the newly formed alkoxide group. The organic phosphorus compound functions to increase the solubility of the magnesium-containing species present.

After formation, the homogenous solution can be optionally treated with a halogenating agent. The halogenating agent can be an organic or inorganic compound containing at least one halogen atom that can be transferrable to a magnesium atom. In particular embodiments, the halogenating agent contains chlorine. In particular embodiments, the halogenating agent is selected from arynoyl chlorides, alkanoyl chlorides, and alkyl chlorides. In certain embodiments, the halogenating agent is selected from benzoyl chloride, furoyl chloride, acetyl chloride, linear or branched $(C_1\text{-}C_6)$ alkyl chloride, and (Ci-Ce) alkanoyl chloride. In one embodiment, the halogenating agent may be phthaloyl chloride. In other embodiments, however, the catalyst composition can be completely phthalate-free. In other embodiments, the halogenating agent is selected from HCl, $TiCl_4R_nTiCl_{4-n}$, $SiCl_4$, $R_nSiCl_{4-n}$, and $R_nAlCl_{4-n}$, wherein R represents an alkyl, cycloalkyl, aromatic or alkoxy, and n is a whole number satisfying the formula 0<n<4. In certain embodiments the ratio of halogenating agent to magnesium compound is at least 1:1 mol ratio.

The molar ratio of the first titanium compound added to the halide-containing magnesium compound may be from about 3:1 to about 15:1, or from about 5:1 to about 10:1.

The magnesium-containing solution formed during the reaction of halide-containing magnesium compound, epoxy compound, organic phosphorus compound and organosilicon compound can be in the form of dispersions, colloids, emulsions, and other two-phase systems. The homogenous solution can be emulsified using conventional emulsion techniques including one or more of agitation, stirring, mixing, high and/or low shear mixing, mixing nozzles, atomizers, membrane emulsification techniques, milling sonication, vibration, microfluidization, and the like.

The magnesium-containing species phase is dispersed within the solvent phase. The size and shape of droplets forming the magnesium phase can be controlled through a combination of adjusting the temperature, adjusting the amount of solvent, adjusting the agitation energy, and including/excluding various additives, including the surface modifier. The temperature during the titanium compounds addition is from about −35° C. to about 15° C. After phase separation and/or titanium compound addition, the mixture is raised to a higher temperature. In one embodiment, the higher temperature is from about 15° C. to about 100° C. In another embodiment, the temperature is from about 20° C. to about 90° C. or from about 50° C. to about 85° C. or from about 60° C. to 85° C. In an embodiment, while the mixture is between the lower and higher temperatures, a surface modifier is added to facilitate formation of spherical droplets of the magnesium phase surrounded by the solvent phase. That is, the addition of a surface modifier can assist in controlling the morphology of the droplets of the magnesium phase.

During addition of titanium halide compound to the magnesium solution which contains associated molecules or groups of molecules of the magnesium alkoxide with coordinated organic phosphorus compound, organosilicon compound and molecules of solvent, the reaction occurs between the magnesium alkoxide and the titanium halide compound forming the magnesium halide and complexes of the magnesium halide with titanium halide compound and the titanium alkoxide.

At the beginning of the reaction (usually at low temperature: (−35 to −20° C.) the new formed associated groups of the magnesium halide molecules and complexes of the magnesium halide with titanium halide compound and the titanium alkoxide are presence in "oil phase-droplets" (higher viscosity liquid than other media (solvent) around). During the continuation of the reaction (the reaction temperature is raised to 0-40° C.) the magnesium halide molecules and complexes of the magnesium halide with titanium halide compound and the titanium alkoxide in the oil phase are crystallized. The crystallization process is usually completed at temperature of 50-100° C. forming the solid intermediate catalyst component.

The morphology of the solid intermediate catalyst component (and the catalyst component) (particle size and shape) depends on many factors including the polarity of solvent, presence of reagents to control precipitation, surfactants, additives and others.

In particular, the size and shape of droplets forming the magnesium phase can be controlled through a combination of adjusting the temperature, amount of solvent, adjusting the agitation energy, and including/excluding various additives, including the surface modifier and temperature of the precipitation.

The catalyst component morphology and catalyst performances are sufficiently controlled by addition of the supportive electron donor (or donors). The supportive electron donor is an organic compound containing oxygen atom and has ability to coordinate to magnesium atom of magnesium in "oil phase-droplets" and allows to control the precipitation process of the solid catalyst component with desired morphology.

In one embodiment, the supportive electron donor only controls the precipitation process and catalyst component morphology and is not incorporated in the catalyst component.

In other embodiment, the supportive electron donor controls the precipitation process and catalyst component morphology and is incorporated in the catalyst component. Therefore, the supportive electron donor and the electron donor both define the catalyst performance in polymerization process. The supportive electron donors are usually weaker than the electron donors.

The combination of the organosilicon compound and the supportive electron donor during the precipitation of the solid catalyst intermediate allow to make the catalyst component with desired granular or spherical shape morphology.

The granular catalyst component morphology can be prepared with raspberry shape, rounded raspberry shape, rounded shape and substantially spherical shape by variation of organosilicon compounds, supportive electron donors and condition of the precipitation the solid catalyst intermediate. The particle sizes of the catalyst component are from about 5 microns to about 70 microns (on a 50% by volume basis) and depends on condition of the precipitation (temperature, agitation speed, solvent and others) and type and amount of the supportive donor.

The supportive electron donor is selected from carboxylic monoesters methyl formate, butyl formate, ethyl acetate, vinyl acetate, propyl acetate, octyl acetate, cyclohexy acetate, ethyl propionate, methyl butyrate, ethyl butyrate, isobutyl butyrate, ethyl valerate, ethyl stearate, methyl chloroacetate, ethyl dichloroacetate, ethyl acrylate, methyl methacrylate, ethyl crotonate, ethyl cyclohexanecarboxylate, methyl benzoate, ethyl benzoate, propyl benzoate, butyl benzoate, octyl benzoate, cyclohexyl benzoate, phenyl benzoate, benzyl benzoate, ethyl p-methoxybenzoate, methyl p-methylbenzoate, ethyl p-t-butylbenzoate, ethyl naphthoate, methyl toluate, ethyl toluate, amyl toluate, ethyl ethylbezoate, methyl anisate, ethyl anisate, or ethyl ethoxybenzoate.

Combining the halide-containing magnesium compound, epoxy compound, organic phosphorus compound, titanium halide and hydrocarbon solvent might create an emulsion with two phases: the solvent phase and the magnesium-titanium oil phase and with proper selection the solvent and reagents. This process can be used to prepare spherical morphology catalyst component. Phase separation is accomplished by proper solvent selection. Solvent selection involves considering one or more of physical properties differences in polarity, density, and surface tension among others causing the separation between the solvent and the magnesium phase. Toluene is an organic solvent diluent that has been used for the formation of solid titanium catalyst components; however, use of toluene does not always promote the formation of two phases. Also, it has been discovered that the use of other alkylbenzene compounds, hexane, and heptane as a solvent or mixture of aromatic and hydrocarbon can be used and result in the formation of a solvent phase and a magnesium phase. The two phases are maintained upon subsequent addition of the titanium compound. The combination of two or more different supportive donors allow producing the solid catalyst component with spherical types.

Di-($C_1$-$C_{12}$)-alkylether with combination of acrylates (surface modifier) are used as the supportive electron donors to prepare the spherical type catalyst component.

General examples of the surface modifier include polymer surfactants, such as polyacrylates, polymethacrylates, polyalkyl methacrylates, or any other surfactant that can stabilize and emulsify. Surfactants are known in the art, and many surfactants are described in McCutcheon's "Volume I: Emulsifiers and Detergents", 2001, North American Edition, published by Manufacturing Confectioner Publishing Co., Glen Rock, N.J., and in particular, pp. 1-233 which describes a number of surfactants and is hereby incorporated by reference for the disclosure in this regard. A polyalkyl methacrylate is a polymer that may contain one or more methacrylate monomers, such as at least two different methacrylate monomers, at least three different methacrylate monomers, etc. Moreover, the acrylate and methacrylate polymers may contain monomers other than acrylate and methacrylate monomers, so long as the polymer surfactant contains at least about 40% by weight acrylate and methacrylate monomers.

Examples of monomers that can be polymerized using known polymerization techniques into polymer surfactants include one or more of acrylate; tert-butyl acrylate; n-hexyl acrylate; methacrylate; methyl methacrylate; ethyl methacrylate; propyl methacrylate; isopropyl methacrylate; n-butyl methacrylate; t-butyl methacrylate; isobutyl methacrylate; pentyl methacrylate; isoamyl methacrylate; n-hexyl methacrylate; isodecyl methacrylate; lauryl methacrylate; stearyl methacrylate; isooctyl acrylate; lauryl acrylate; stearyl acrylate; cyclohexyl acrylate; cyclohexyl methacrylate; methoxyethyl acrylate; isobenzyl acrylate; isodecyl acrylate; n-dodecyl acrylate; benzyl acrylate; isobornyl acrylate; isobornyl acrylate; isobornyl methacrylate; 2-hydroxyethyl acrylate; 2-hydroxypropyl acrylate; 2-methoxyethyl acrylate; 2-methoxybutyl acrylate; 2-(2-ethoxyethoxy)ethyl acrylate; 2-phenoxyethyl acrylate; tetrahydrofurfuryl acrylate; 2-(2-phenoxyethoxy)ethyl acrylate; methoxylated tripropylene glycol monacrylate; 1,6-hexanediol diacrylate; ethylene glycol dimethacrylate; diethylene glycol dimethacrylate; triethylene glycol dimethacrylate; polyethylene glycol dimethacrylate; butylene glycol dimethacrylate; trimethylolpropane-3-ethoxylate triacrylate; 1,4-butanediol diacrylate; 1,9-nonanediol diacrylate; neopentyl glycol diacrylate; tripropylene glycol diacrylate; tetraethylene glycol diacrylate; heptapropylene glycol diacrylate; trimethylol propane triacrylate; ethoxylated trimethylol propane triacrylate; pentaerythritol triacrylate; trimethylolpropane trimethacrylate; tripropylene glycol diacrylate; pentaerythritol tetraacrylate; glyceryl propoxy triacrylate; tris(acryloyloxyethyl)phosphate; 1-acryloxy-3-methacryloxy glycerol; 2-methacryloxy-N-ethyl morpholine; and allyl methacrylate, and the like.

In certain embodiments, the surface modifier is selected from poly(($C_1$-$C_6$) alkyl) acrylate, a poly(($C_1$-$C_6$) alkyl) methacrylate, and a copolymer of poly(($C_1$-$C_6$) alkyl) acrylate and poly(($C_1$-$C_6$) alkyl) methacrylate. In embodiments, a ratio of the surface modifier to halide-containing magnesium compound is from 1:10 to 2:1 wt % or from 1:5 to 1:1 wt %.

Examples of polymer surfactants that are commercially available include those under the trade designation VISCOPLEX® available from RohMax Additives, GmbH, including those having product designations 1-254, 1-256 and those under the trade designations CARBOPOL® and PEMULEN® available from Noveon/Lubrizol.

The polymer surfactant is typically added in a mixture with an organic solvent. When added as a mixture with an organic solvent, the weight ratio of surfactant to organic solvent is from about 1:20 to about 2:1. In another embodiment, the weight ratio of surfactant to organic solvent is from about 1:10 to about 1:1. In yet another embodiment, the weight ratio of surfactant to organic solvent is from about 1:4 to about 1:2.

Treatment with the second titanium compound may include adding the second titanium halide compound and the second electron donor to a solution containing the precipitate to form a solid catalyst composition, and then bringing a temperature of the solid catalyst composition to from 80° C. to 150° C. and further treating with the second titanium compound to form the solid catalyst component. In one embodiment, the treatment may include more than one second electron donor. For example, a plurality of electron donors can occur during treatment with the second titanium compound. In another embodiment, the second titanium compound treatment includes the steps of filtering out the precipitate, adding the second titanium compound and the second electron donor in a solvent to the precipitate to form a solid catalyst composition, and bringing a temperature of the solid catalyst composition to from 80° C. to 150° C. In another embodiment, the second titanium compound treatment includes the steps of adding the second titanium compound to a solution containing the precipitate; and then bringing a temperature of the solid catalyst composition to from 80° C. to 150° C. and further treating with the second titanium compound and the second electron donor to form the solid catalyst component.

Treatment with the second titanium compound may include adding the second titanium halide compound and the second electron donor to a solution containing the precipitate to form a solid catalyst composition, and then bringing a temperature of the solid catalyst composition to from 80° C. to 150° C. and further treating with the second titanium compound to form the solid catalyst component. In another embodiment, the second titanium compound treatment includes the steps of filtering out the precipitate, adding the second titanium compound and the second electron donor in a solvent to the precipitate to form a solid catalyst composition, and bringing a temperature of the solid catalyst composition to from 80° C. to 150° C. In another embodiment, the second titanium compound treatment includes the steps of adding the second titanium compound to a solution containing the precipitate; and then bringing a temperature of the solid catalyst composition to from 80° C. to 150° C. and further treating with the second titanium compound and the second electron donor to form the solid catalyst component.

During this treatment, the supportive electron donor partly or fully is removed from the catalyst component and the electron donors adjust the coordination to magnesium halides resulting in increased catalyst activity.

In one embodiment, for instance, a solid catalyst component can be made in accordance with the present disclosure by combining a magnesium halide, such as magnesium chloride with an epoxy compound. The epoxy compound, for instance, can be epichlorohydrin. The magnesium halide and the epoxy compound can be combined together at a molar ratio of from about 0.5:1 to about 1:0.5, such as from about 0.8:1.2 to about 1.2:0.8. In one embodiment, for instance, the magnesium halide and the epoxy compound can be combined together in approximately a 1 to 1 molar ratio. The magnesium halide and epoxy compound can be combined together in the presence of a phosphate such as tributyl phosphate and a solvent such as toluene. In addition, an aluminum alkoxide surfactant may be present, such as aluminum alkoxide/isopropoxide.

A monoester, such as ethylbenzoate and a silicate, such as tetraethylorthosilicate can be added to the above composition in addition to a titanium halide such as titaniumtetrachloride to cause a precipitate to form. In one embodiment, complexes of the magnesium halide with the monoester, the titanium chloride can form including Cl$_3$—Ti—O—CH(CH$_2$Cl)$_2$.

The above precipitate can then be treated with a second internal donor, such as an aryldiester and optionally in the presence with a titanium halide. The resulting solid catalyst component can be washed and used as desired.

In general, the resulting solid catalyst component contains a magnesium halide, a titanium halide, the first internal donor or supportive donor, and the second internal donor. In addition, the solid catalyst component can contain residual amounts of an aluminum alkoxide, the organosilicon compound and the phosphorus compound. For example, the amount of the aluminum alkoxide and/or the organosilicon compound present in the final catalyst can be generally greater than about 0.001% by weight, such as greater than about 0.01% by weight, such as greater than about 0.1% by weight and generally less than about 1% by weight, such as less than about 0.5% by weight, such as less than about 0.3% by weight. The solid catalyst component can also contain the phosphorous compound generally in an amount greater than about 0.1% by weight, such as in an amount greater than about 0.2% by weight, such as in an amount greater than about 0.3% by weight, and generally less than about 1% by weight, such as less than about 0.5% by weight.

In an alternative embodiment, especially in order to form spherical particles, the first internal electron donor may include not only a monoester but also a dialklyether. In addition, the first internal electron donor can be combined into the catalyst composition with a spherical-promoting surfactant, such as an acrylate surfactant. In one embodiment, for instance, the surfactant may comprise a polyalkyl methacylate.

The solid catalyst component of the present disclosure is produced with many beneficial properties and characteristics. For instance, in one embodiment, the catalyst component can be made with a relatively high surface area. For example, the BET surface area of the catalyst can be greater than about 100 m$^2$/g, such as greater than about 200 m$^2$/g, such as greater than about 300 m$^2$/g, such as greater than about 400 m$^2$/g and generally less than about 700 m$^2$/g, such as less than about 600 m$^2$/g.

The solid catalyst component may be used after with an inorganic or organic compound such as a silicon compound or an aluminum compound.

The catalyst system may contain at least one organoaluminum compound in addition to the solid catalyst component. Compounds having at least one aluminum-carbon bond in the molecule can be used as the organoaluminum compound. Examples of organoaluminum compounds include those of Formula:

$$AlR_nX_{3-n}$$

wherein, R independently represents a hydrocarbon group usually having 1 to about 20 carbon atoms, X represents a halogen atom, and $0<n\le3$.

Specific examples of the organoaluminum compounds include, but are not limited to, trialkyl aluminums such as triethyl aluminum, tributyl aluminum and trihexyl aluminum; trialkenyl aluminums such as triisoprenyl aluminum; dialkyl aluminum halides such as diethyl aluminum chloride, dibutyl aluminum chloride and diethyl aluminum bromide; alkyl aluminum sesquihalides such as ethyl aluminum sesquichloride, butyl aluminum sesquichloride and ethyl aluminum sesquibromide; alkyl aluminum dihalides such as ethyl aluminum dichloride, propyl aluminum dichloride and butyl aluminum dibromide; dialkyl aluminum hydrides such as diethyl aluminum hydride and dibutyl aluminum hydride; and other partially hydrogenated alkyl aluminum such as ethyl aluminum dihydride, and propyl aluminum dihydride.

The organoaluminum compound can be used in the catalyst system in an amount that the mole ratio of aluminum to titanium (from the solid catalyst component) is from about 5 to about 1. In another embodiment, the mole ratio of aluminum to titanium in the catalyst system is from about 10 to about 700. In yet another embodiment, the mole ratio of aluminum to titanium in the catalyst system is from about 25 to about 400.

The catalyst system may contain one or more selectivity control agents (SCA) in addition to the solid catalyst component. In one embodiment, the selectivity control agent can comprise one or more organosilicon compounds, such as one or more silane compounds. This organosilicon compound can also function as an external electron donor. The organosilicon compound contains silicon having at least one hydrogen ligand (hydrocarbon group). General examples of hydrocarbon groups include alkyl groups, cycloalkyl groups, (cycloalkyl)methylene groups, alkene groups, aromatic groups, and the like.

The organosilicon compound, when used as an external electron donor serving as one component of a Ziegler-Natta catalyst system for olefin polymerization, contributes to the ability to obtain a polymer (at least a portion of which is polyolefin) having a controllable molecular weight distribution and controllable crystallinity while retaining high performance with respect to catalytic activity.

The organosilicon compound is used in the catalyst system in an amount such that the mole ratio of the organoaluminum compound to the organosilicon compound is from about 2 to about 90. In another embodiment, the mole ratio of the organoaluminum compound to the organosilicon compound is from about 5 to about 70. In yet another embodiment, the mole ration of the organoaluminum compound to the organosilicon compound is from about 7 to about 35.

In one embodiment, the organosilicon compound is represented by Formula:

$$R_n Si(OR')_{4-n}$$

wherein each R and R' independently represent a hydrocarbon group, and n is 0≤n<4.

Specific examples of the organosilicon compound include, but are not limited to trimethylmethoxysilane, trimethylethoxysilane, dimethyldimethoxysilane, dimethyldiethoxysilane, diisopropyldimethoxysilane, diisobutyldimethoxysilane, t-butylmethyldimethoxysilane, t-butylmethyldiethoxysilane, t-amylmethyldiethoxysilane, dicyclopentyldimethoxysilane, diphenyldimethoxysilane, phenylmethyldimethoxysilane, diphenyldiethoxysilane, bis-o-tolydimethoxysilane, bis-m-tolydimethoxysilane, bis-p-tolydimethoxysilane, bis-p-tolydiethoxysilane, bisethylphenyldimethoxysilane, dicyclohexyldimethoxysilane, cyclohexylmethyldimethoxysilane, cyclohexylmethyldiethoxysilane, ethyltrimethoxysilane, ethyltriethoxysilane, vinyltrimethoxysilane, methyltrimethoxysilane, n-propyltriethoxysilane, decyltrimethoxysilane, decyltriethoxysilane, phenyltrimethoxysilane, γ-chloropropyltrimethoxysilane, methyltriethoxysilane, ethyltriethoxysilane, vinyltriethoxysilane, t-butyltriethoxysilane, nbutyltriethoxysilane, isobutyltriethoxysilane, phenyltriethoxysilane, γ-amniopropyltriethoxysilane, cholotriethoxysilane, ethyltriisopropoxysilane, vinyltributoxysilane, cyclohexyltrimethoxysilane, cyclohexyltriethoxysilane, 2-norbornanetrimethoxysilane, 2-norboranetriethoxysilane, 2-norboranemethyldimethoxysilane, ethyl silicate, butyl silicate, trimethylphenoxysilane, and methyltriallyloxysilane.

In another embodiment, the organosilicon compound is represented by Formula:

$$SiRR'_m(OR'')_{3-m}$$

wherein, 0≤m<3, such as 0≤m<2; and R independently represents a cyclic hydrocarbon or substituted cyclic hydrocarbon group. Specific examples of the group R include, but are not limited to cyclopropyl; cyclobutyl; cyclopentyl; 2-methylcyclopentyl; 3-methylcyclopentyl; 2-ethylcyclopentyl; 3-propylcyclopentyl; 3-isopropylcyclopentyl; 3-butylcyclopentyl; 3-tertiary-butyl cyclopentyl; 2,2-dimethylcyclopentyl; 2,3-dimethylcyclopentyl; 2,5-dimethylcyclopentyl; 2,2,5-trimethylcyclopentyl; 2,3,4,5-tetramethylcyclopentyl; 2,2,5,5-tetramethylcyclopentyl; 1-cyclopentylpropyl; 1-methyl-1-cyclopentylethyl; cyclopentenyl; 2-cyclopentenyl; 3-cyclopentenyl; 2-methyl-1-cyclopentenyl; 2-methyl-3-cyclopentenyl; 3-methyl-3-cyclopentenyl; 2-ethyl-3-cyclopentenyl; 2,2-dimethyl-3-cyclopentenyl; 2,5-dimethyl-3-cyclopentenyl; 2,3,4,5-tetramethyl-3-cyclopentenyl; 2,2,5,5-tetramethyl-3-cyclopentenyl; 1,3-cyclopentadienyl; 2,4-cyclopentadienyl; 1,4-cyclopentadienyl; 2-methyl-1,3-cyclopentadienyl; 2-methyl-2,4-cyclopentadienyl; 3-methyl-2,4-cyclopentadienyl; 2-ethyl-2,4-cyclopentadienyl; 2,2-dimethyl-2,4-cyclopentadienyl; 2,3-dimethyl-2,4-cyclopentadienyl; 2,5-dimethyl-2,4-cyclopentadienyl; 2,3,4,5-tetramethyl-2,4-cyclopentadienyl; indenyl; 2-methylindenyl; 2-ethylindenyl; 2-indenyl; 1-methyl-2-indenyl; 1,3-dimethyl-2-indenyl; indanyl; 2-methylindanyl; 2-indanyl; 1,3-dimethyl-2-indanyl; 4,5,6, 7-tetrahydroindenyl; 4,5,6, 7-tetrahydro-2-indenyl; 4,5,6, 7-tetrahydro-1-methyl-2-indenyl; 4,5,6, 7-tetrahydro-1,3-dimethyl-2-indenyl; fluorenyl groups; cyclohexyl; methylcyclohexyl; ethylcyclohexyl; propylcyclohexyl; isopropylcyclohexyl; n-butylcyclohexyl; tertiary-butyl cyclohexyl; dimethylcyclohexyl; and trimethylcyclohexyl.

In the Formula: $SiRR'_m(OR'')_{3-m}$, R' and R" are identical or different and each represents a hydrocarbon. Examples of R' and R" are alkyl, cycloalkyl, aryl and aralkyl groups having 3 or more carbon atoms. Furthermore, R and R' may be bridged by an alkyl group, etc. General examples of organosilicon compounds are those of formula (VIII) in which R is cyclopentyl group, R' is an alkyl group such as methyl or cyclopentyl group, and R" is an alkyl group, particularly a methyl or ethyl group.

Specific examples of organosilicon compounds of Formula $SiRR'_m(OR'')_{3-m}$ include, but are not limited to trialkoxysilanes such as cyclopropyltrimethoxysilane, cyclobutyltrimethoxysilane, cyclopentyltrimethoxysilane, 2-methylcyclopentyltrimethoxysilane, 2,3-dimethylcyclopentyltrimethoxysilane, 2,5-dimethylcyclopentyltrimethoxysilane, cyclopentyltriethoxysilane, cyclopentenyltrimethoxysilane, 3-cyclopentenyltrimethoxysilane, 2,4-cyclopentadienyltrimethoxysilane, indenyltrimethoxysilane and fluorenyltrimethoxysilane; dialkoxysilanes such as dicyclopentyldimethoxysilane, bis(2-methylcyclopentyl)dimethoxysilane, bis(3-tertiary-butylcyclopentyl)dimethoxysilane, bis(2,3-dimethylcyclopentyl)dimethoxysilane, bis(2,5-dimethylcyclopentyl)dimethoxysilane, dicyclopentyldiethoxysilane, dicyclobutyldiethoxysilane, cyclopropylcyclobutyldiethoxysilane, dicyclopentenyldimethoxysilane, di(3-cyclopentenyl)dimethoxysilane, bis(2,5-dimethyl-3-cyclopentenyl)dimethoxysilane, di-2,4-cyclopentadienyl)dimethoxysilane, bis(2,5-dimethyl-2,4-cyclopentadienyl)dimethoxysilane, bis(1-methyl-1-cyclopentylethyl)dimethoxysilane, cyclopentylcyclopentenyldimethoxysilane, cyclopentylcyclopentadienyldimethoxysilane, diindenyldimethoxysilane, bis(1,3-dimethyl-2-indenyl)dimethoxysilane, cyclopentadienylindenyldimethoxysilane, difluorenyldimethoxysilane, cyclopentylfluorenyldimethoxysilane and indenylfluorenyldimethoxysilane; monoalkoxysilanes such as tricyclopentylmethoxysilane, tricyclopentenylmethoxysilane, tricyclopentadienylmethoxysilane, tricyclopentyletyoxysilane, dicyclopentylmethylmethoxysilane, dicyclopentylethylmethoxysilane, dicyclopentylmethylethoxysilane, cyclopentyldimethylmethoxysilane, cyclopentyldiethylmethoxysilane, cyclopentyldimethylethoxysilane, bis(2,5-dimethylcyclopentyl)cyclopentylmethoxysilane, dicyclopentylcyclopentenylmethoxysilane, dicyclopentylcyclopentenadienylmethoxysilane and diindenylcyclopentylmethoxysilane; and ethylenebis-cyclopentyldimethoxysilane.

In one embodiment, one or more selectivity control agents are present in the catalyst system. Particularly preferred selectivity control agents include dimethyldimethoxysilane, n-propyltrimethoxysilane, methylcyclohexyldimethoxysilane, diisopropyldimethoxysilane, n-propyltriethoxysilane, bis(perhydroisoquinolino) dimethoxysilane, 2,2,6,6-tetramethylpiperidine, or mixtures thereof.

In one embodiment, one or more selectivity control agents may be used in conjunction with an activity limiting agent (ALA). The activity limiting agent can be an aliphatic ester. The aliphatic ester may be a $C_4$-$C_{30}$ aliphatic acid ester, may be a mono- or a poly-(two or more) ester, may be straight chain or branched, may be saturated or unsaturated, and any combination thereof. The $C_4$-$C_{30}$ aliphatic acid ester may also be substituted with one or more Group 14, 15 or 16 heteroatom containing substituents. Nonlimiting examples of suitable $C_4$-$C_{30}$ aliphatic acid esters include $C_{1-20}$ alkyl esters of aliphatic $C_{4-30}$ monocarboxylic acids, $C_{1-20}$ alkyl esters of aliphatic $C_{8-20}$ monocarboxylic acids, $C_{1-4}$ allyl mono- and diesters of aliphatic $C_{4-20}$ monocarboxylic acids and dicarboxylic acids, $C_{1-4}$alkyl esters of aliphatic $C_{5-20}$ monocarboxylic acids and dicarboxylic acids, and $C_{4-20}$ alkyl mono- or polycarboxylate derivatives of $C_{2-100}$(poly)glycols or $C_{2-100}$(poly)glycol ethers. In a further embodiment, the $C_4$-$C_{30}$ aliphatic acid ester may be isopropyl myristate, di-n-butyl sebacate, (polyxalkylene glycol) mono- or diacetates, (polyxalkylene glycol) mono- or dimyristates, (polyxalkylene glycol) mono- or di-laurates, (poly)(alkylene glycol) mono- or di-oleates, glyceryl tri (acetate), glyceryl tri-ester of $C_{2-40}$ aliphatic carboxylic acids, and mixtures thereof. In a further embodiment, the $C_{4-C30}$ aliphatic ester is isopropyl myristate or di-n-butyl sebacate.

In one embodiment, the ALA is a non-ester composition. As used herein, a "non-ester composition" is an atom, molecule, or compound that is free of an ester functional group. In other words, the "non-ester composition" does not contain the following functional group.

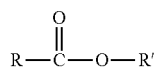

In one embodiment, the non-ester composition may be a dialkyl diether compound or an amine compound. The dialkyl diether compound can be represented by the following formula,

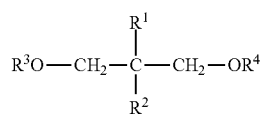

wherein $R^1$ $R^4$ are independently of one another an alkyl, aryl or aralkyl group having up to 20 carbon atoms, which may optionally contain a group 14, 15, 16, or 17 heteroatom, provided that $R^1$ and $R^2$ may be a hydrogen atom. Nonlimiting examples of suitable dialkyl ether compounds include dimethyl ether, diethyl ether, dibutyl ether, methyl ethyl ether, methyl butyl ether, methyl cyclohexyl ether, 2,2-dimethyl-1,3-dimethoxypropane, 2,2-diethyl-1,3-dimethoxypropane, 2,2-di-n-butyl-1,3-dimethoxypropane, 2,2-diisobutyl-1,3-dimethoxypropane, 2-ethyl-2-n-butyl-1,3-dimethoxypropane, 2-n-propyl-2-cyclopentyl-1,3-dimethoxypropane, 2,2-dimethyl-1,3-diethoxypropane, 2-isopropyl-2-isobutyl-1,3-dimethoxypropane, 2,2-dicyclopentyl-1,3-dimethoxypropane, 2-n-propyl-2-cyclohexyl-1, 3-diethoxypropane, and 9,9-bis(methoxymethyl)fluorene. In a further embodiment, the dialkyl ether compound is 2,2-diisobutyl-1,3-dimethoxypropane.

In one embodiment, the non-ester composition is an amine compound. Nonlimiting examples of suitable amine compounds include 2,6-substituted piperidines such as 2,6-dimethylpiperidine and 2,2,6,6-tetramethylpiperidine and 2,5-substituted piperidines. In a further embodiment, the piperidine compound is 2,2,6,6-tetramethylpiperidine.

For ALA's that contains more than one carboxylate groups, all the carboxylate groups are considered effective components. For example, a sebacate molecule contains two carboxylate functional groups is considered to have two effective functional molecules.

As described above, in one embodiment, the activity limiting agent is a C4 to C30 Aliphatic acid ester. Alternatively, the activity limiting agent may comprise a diether or a poly(alkene glycol) ester of a C4 to C30 aliphatic acid. Particular activity limiting agents that may be incorporated into the catalyst system include isopropyl myristate, di-n-butyl sebacate, ethyl 4-ethoxybenzoate, propoxylated (POE) coco fatty acid esters such as containing 10 to 20 mols of POE, a poly(ethylene)glycol coco fatty acid ester, or mixtures thereof.

An especially preferred combination of SCA/ALA components is a mixture of an alkoxy silane selected from the group consisting of dicyclopentyldimethoxysilane, methylcyclohexyl-dimethoxysilane, and n-propyltrimethoxysilane with an ester which is isopropyl myristate, di(n-butyl) sebacate, (poly)(ethylene glycol) monolaurate, (polyxalkene glycol) dioleate, (poly)(ethylene glycol) methyl ether laurate, glyceryl tri(acetate), or a mixture thereof.

Preferred SCA/ALA mixtures according to the invention are those comprising from 1 to 99.9, more preferably from 30 to 99, and most preferably from 50 to 98 equivalent percent of one or more ALA compounds, and correspondingly from 99 to 0.1, more preferably from 70 to 1, most preferably from 50 to 2 equivalent percent of one or more alkoxysilane compounds. Regardless of the foregoing range of components, it is to be understood by the skilled artisan that the normalized polymerization activity at an elevated temperature should be less than that obtainable at 67° C. and less than that obtainable if the alkoxysilane alone were employed alone in the same total SCA molar amount.

The total molar quantity of the SCA mixture employed in the present invention based on moles of transition metal is desirably from 0.1 to 500, more desirably from 0.5 to 100 and most preferably from 1.0 to 50. With respect to quantity of ALA, the corresponding molar ratio based on transition metal is desirably from 1 to 10,000, preferably from 2 to 1000, and most preferably from 5 to 100.

Catalyst particle morphology is indicative of the polymer particle morphology produced therefrom. The three parameters of polymer particle morphology (sphericity, symmetry and aspect ratio) may be determined using a Camsizer instrument. Camsizer Characteristics:

Sphericity $$SPHT = \frac{4\pi A}{P^2} = \text{Circularity } 2(ISO9276\text{-}6),$$

where:
P is the measured perimeter/circumference of a particle projection; and
A is the measured area covered by a particle projection.
P is the measured perimeter/circumference of a particle projection; and
A is the measured area covered by a particle projection.

For an ideal sphere, SPHT is defined as 1. Otherwise, the value is less than 1.

The symmetry is defined as:

$$Symm_{0,3} = \frac{1}{2}\left(1 + \min\left(\frac{r_1}{r_2}\right)\right)$$

where, $r_1$ and $r_2$ are distance from the centre of area to the borders in the measuring direction. For asymmetric particles Symm is less than 1. If the centre of the area is outside the particle, i.e. $\frac{r_1}{r_2} < 0$, the Symm is less than 0.5

$w_{Ma}=r_1+r_2$, or "Symm," is the minimum value of measured set of symmetry values from different directions.

Aspect Ratio:

$$b/l_{0,2,3} = \frac{x_{c\,min}}{x_{Fe\,max}}$$

where $x_{c\,min}$ and $x_{Fe\,max}$ out of the measured set of $x_c$ and $x_{Fe}$ values.

The catalyst morphology characteristics such as aspect ratio ("B/L3") can be used for characterization of polymer morphology. In some processes the aspect ratio is higher than 0.6, or higher than 0.7, or higher than 0.8, or higher than 0.90.

The particle size of the resulting catalyst component can vary depending upon the process conditions and the desired result. In general, the $D_{50}$ particle size can be greater than about 5 microns, such as greater than about 10 microns, such as greater than about 20 microns, such as greater than about 30 microns, such as greater than about 40 microns, such as greater than about 50 microns, such as greater than about 60 microns, and generally less than about 70 microns, such as less than about 50 microns, such as less than about 30 microns, such as less than about 25 microns.

Polymerization of olefins can be carried out in the presence of the catalyst systems as prepared and described above. Various different olefins can be polymerized in accordance with the present disclosure. For example, catalyst systems of the present disclosure can be used to polymerize ethylene, propylene, and the like. The catalyst systems can also be used to produce homopolymers and copolymers. Generally speaking, an olefin monomer, such as propylene, is contacted with the catalyst system described above under suitable conditions to form desired polymer products. In one embodiment, preliminary polymerization described below is carried out before the main polymerization. In another embodiment, polymerization is carried out without preliminary polymerization. In yet another embodiment, the formation of a polypropylene-co-polymer is carried out using at least two polymerization zones.

Of particular advantage, the catalyst component of the present disclosure is well suited for use in all different types of polymerization processes. For instance, the catalyst component of the present disclosure can be used in bulk loop polymerization processes, gas phase processes, and the like. The catalyst component can also be used in a slurry process.

In preliminary polymerization, the solid catalyst component is usually employed in combination with at least a portion of the organoaluminum compound. This may be carried out in the presence of part or the whole of the organosilicon compound (external electron donor compound). The concentration of the catalyst system used in the preliminary polymerization may be much higher than that in the reaction system of the main polymerization.

In preliminary polymerization, the concentration of the solid catalyst component in the preliminary polymerization is usually from about 0.01 to about 200 millimoles, or from about 0.05 to about 100 millimoles, calculated as titanium atoms per liter of an inert hydrocarbon medium described below. In one embodiment, the preliminary polymerization is carried out by adding propylene or a mixture of propylene with another olefin and the above catalyst system ingredients to an inert hydrocarbon medium and polymerizing the olefins under mild conditions.

Specific examples of the inert hydrocarbon medium include, but are not limited to aliphatic hydrocarbons such as propane, butane, pentane, hexane, heptanes, octane, decane, dodecane and kerosene; alicyclic hydrocarbons such as cyclopentane, cyclohexane and methylcyclopentane; aromatic hydrocarbons such as benzene, toluene and xylene; and mixtures thereof. In certain embodiments, a liquid olefin may be used in place of part or the whole of the inert hydrocarbon medium.

The olefin used in the preliminary polymerization may be the same as, or different from, an olefin to be used in the main polymerization.

The reaction temperature for the preliminary polymerization is sufficient for the resulting preliminary polymer to not substantially dissolve in the inert hydrocarbon medium. In one embodiment, the temperature is from about −20° C. to about 100° C. In another embodiment, the temperature is from about −10° C. to about 80° C. In yet another embodiment, the temperature is from about 0° C. to about 40° C.

Optionally, a molecular-weight controlling agent, such as hydrogen, may be used in the preliminary polymerization. The molecular weight controlling agent is used in such an amount that the polymer obtained by the preliminary polymerization has an intrinsic viscosity, measured in decaliter at 135° C., of at least about 0.2 dl/g, or from about 0.5 to 10 dl/g.

In one embodiment, the preliminary polymerization is carried out so that from about 0.1 g to about 1,000 g of a polymer is formed per gram of the solid catalyst component of the catalyst system. In another embodiment, the preliminary polymerization is carried out so that from about 0.3 g to about 500 g of a polymer is formed per gram of the solid catalyst component. If the amount of the polymer formed by the preliminary polymerization is too large, the efficiency of producing the olefin polymer in the main polymerization may sometimes decrease, and when the resulting olefin polymer is molded into a film or another article, fish eyes tend to occur in the molded article. The preliminary polymerization may be carried out batchwise or continuously.

After the preliminary polymerization conducted as above, or without performing any preliminary polymerization, the main polymerization of the propylene is carried out in the presence of the above-described polymerization catalyst system formed from the solid catalyst component, the organoaluminum compound and the organosilicon compound (external electron donor compound).

Examples of other olefins that can be used in the main polymerization with propylene are α-olefins having 2 to 20 carbon atoms such as ethylene, propylene, 1-butene, 4-methyl-1-pentene, 1-pentene, 1-octene, 1-hexene, 3-methyl-1-pentene, 3-methyl-1-butene, 1-decene, 1-tetradecene, 1-eicosene, and vinylcyclohexane. In illustrative processes, these α-olefins may be used individually or in any combination.

In one embodiment, propylene is homopolymerized, or a mixed olefin containing propylene as a main component is copolymerized. When the mixed olefin is used, the proportion of propylene as the main component is usually at least about 50 mole %, or at least about 70 mole %.

By performing the preliminary polymerization, the catalyst system in the main polymerization can be adjusted in the degree of activity. This adjustment tends to result in a powdery polymer having a high bulk density. Furthermore, when the preliminary polymerization is carried out, the particles shape of the resulting polymer becomes spherical, and in the case of slurry polymerization, the slurry attains excellent characteristics while in the case of gas phase polymerization, the polymer seed bed attains excellent characteristics. Furthermore, in these embodiments, a polymer having a high stereoregularity index can be produced with a high catalytic efficiency by polymerizing an α-olefin having at least 3 carbon atoms. Accordingly, when producing the propylene copolymer, the resulting copolymer powder or the copolymer becomes easy to handle.

In the copolymerization of the propylene, a polyunsaturated compound such as conjugated diene or non-conjugated diene may be used as a comonomer. Examples of comonomers include styrene, butadiene, acrylonitrile, acrylamide, α-methyl styrene, chlorostyrene, vinyl toluene, divinyl benzene, diallyphthalate, alkyl methacrylates and alkyl acrylates. In one embodiment, the comonomers include thermoplastic and elastomeric monomers. The main polymerization of an olefin is carried out usually in the gaseous or liquid phase. In one embodiment, polymerization (main polymerization) employs a catalyst system containing the solid catalyst component in an amount from about 0.001 to about 0.75 millimoles calculated as Ti atom per liter of the volume of the polymerization zone, the organoaluminum compound in an amount from about 1 to about 2,000 moles per mole of titanium atoms in the solid catalyst component, and the organosilicon compound in an amount from about 0.001 to about 10 moles calculated as Si atoms in the organosilicon compound per mole of the metal atoms in the organoaluminum compound. In another embodiment, polymerization employs a catalyst system containing the solid catalyst component in an amount of from 0.005 to about 0.5 milimoles calculated as Ti atom per liter of the volume of the polymerization zone, the organoaluminum compound in an amount from about 5 to about 500 moles per mole of titanium atoms in the solid catalyst component, and the organosilicon compound in an amount from about 0.01 to about 2 moles calculated as Si atoms in the organosilicon compound per mole of the metal atoms in the organoaluminum compound. In yet another embodiment, polymerization employs a catalyst system containing the alkyl benzoate derivative in an amount from about 0.005 to about 1 mole calculated as Si atoms in the organosilicon compound per mole of the metal atoms in the organoaluminum compound.

When the organoaluminum compound and the organosilicon compound are used partially in the preliminary polymerization, the catalyst system subjected to the preliminary polymerization is used together with the remainder of the catalyst system components. The catalyst system subjected to the preliminary polymerization may contain the preliminary polymerization product.

The use of hydrogen at the time of polymerization promotes and contributes to control of the molecular weight of the resulting polymer, and the polymer obtained may have a high melt flow rate. In this case, the stereoregularity index of the resulting polymer and the activity of the catalyst system can be increased according to the above methods.

In one embodiment, the polymerization temperature is from about 20° C. to about 170° C. In another embodiment, the polymerization temperature is from about 50° C. to about 165° C. In one embodiment, the polymerization pressure is typically from atmospheric pressure to about 100 kg/cm$^2$. In another embodiment, the polymerization pressure is typically from about 2 kg/cm$^2$ to about 50 kg/cm$^2$. The main polymerization may be carried out batchwise, semi-continuously or continuously. The polymerization may also be carried out in two or more stages under different reaction conditions.

The olefin polymer so obtained may be a homopolymer, a random copolymer, a block copolymer or an impact copolymer. The impact copolymer contains an intimate mixture of a polyolefin homopolymer and a polyolefin rubber. Examples of polyolefin rubbers include ethylene propylene rubber (EPR) such as ethylene propylene methylene copolymer rubber (EPM) and ethylene propylene diene methylene terpolymer rubber (EPDM).

The olefin polymer obtained by using the catalyst system has a very small amount of an amorphous polymer component and therefore a small amount of a hydrocarbon-soluble component. Accordingly, a film molded from the resultant polymer has low surface tackiness.

The polyolefin obtained by the polymerization process is excellent in particle size distribution, particle diameter and bulk density, and the copolyolefin obtained has a narrow composition distribution. In an impact copolymer, excellent fluidity, low temperature resistance, and a desired balance between stiffness and elasticity can be obtained.

In one embodiment, propylene and an α-olefin having 2 or from about 4 to about 20 carbon atoms are copolymerized in the presence of the catalyst system described above. The catalyst system may be one subjected to the preliminary polymerization described above. In another embodiment, propylene and an ethylene rubber are formed in two reactors coupled in series to form an impact polymer.

The α-olefin having 2 carbon atoms is ethylene, and examples of the α-olefin having about 4 to about 20 carbon atoms are 1-butene, 1-pentene, 4-methyl-1-pentene, 1-octene, 1-hexene, 3-methyl-1-pentene, 3-methyl-1-butene, 1-decene, vinylcyclohexane, 1-tetradecene, and the like.

In the main polymerization, propylene may be copolymerized with two or more such α-olefins. For example, it is possible to copolymerize propylene with ethylene and 1-butene. In one embodiment, propylene is copolymerized with ethylene, 1-butene or ethylene and 1-butene.

Block copolymerization of propylene and another α-olefin may be carried out in two stages. The polymerization in a first stage may be the homopolymerization of propylene or the copolymerization of propylene with the other α-olefin. In one embodiment, the amount of the monomers polymerized in the first stage is from about 50 to about 95% by weight. In another embodiment, the amount of the monomers polymerized in the first stage is from about 60 to about 90% by weight. This first stage polymerization may be carried out in two or more stages under the same or different polymerization conditions.

In one embodiment, the polymerization in a second stage is carried out such that the mole ratio of propylene to the other α-olefin(s) is from about 10/90 to about 90/10. In another embodiment, the polymerization in a second stage is carried out such that the mole ratio of propylene to the other α-olefin(s) is from about 20/80 to about 80/20. In yet another embodiment, the polymerization in a second stage is carried out such that the mole ratio of propylene to the other α-olefin(s) is from about 30/70 to about 70/30. Producing a crystalline polymer or copolymer of another α-olefin may be provided in the second polymerization stage.

The propylene copolymer so obtained may be a random copolymer or the above described block copolymer. This propylene copolymer can contain from about 7 to about 50 mole % of units derived from the α-olefin having 2 or from about 4 to about 20 carbon atoms. In one embodiment, a propylene random copolymer contains from about 7 to about 20 mole % of units derived from the α-olefin having 2 or from about 4 to about 20 carbon atoms. In another embodiment, the propylene block copolymer contains from about 10 to about 50 mole % of units derived from the α-olefin having 2 or 4-20 carbon atoms.

In another embodiment, copolymers made with the catalyst system contain from about 50% to about 99% by weight poly-α-olefins and from about 1% to about 50% by weight comonomers (such as thermoplastic or elastomeric monomers). In another embodiment, copolymers made with the catalyst system contain from about 75% to about 98% by weight poly-α-olefins and from about 2% to about 25% by weight comonomers.

It should be understood that where there is no reference to the polyunsaturated compound that can be used, the method of polymerization, the amount of the catalyst system and the polymerization conditions, the same description as the above embodiment are applicable.

In one embodiment, the catalyst efficiency (measured as kilogram of polymer produced per gram of catalyst) of the catalyst system is at least about 30 kg/g/h. The catalyst deficiency, for instance, can be higher than about 60 kg/g/h, such as greater than about 80 kg/g/h, such as greater than about 100 kg/g/h, such as greater than about 140 kg/g/h.

The catalysts/methods discussed above can in some instances lead to the production of poly-α-olefins having melt flow rates ("MFR", g/10 minutes) from about 0.01 to about 500 g/10 min, such as from about 0.1 to about 400 g/10 min. The MFR is measured according to ASTM standard In another embodiment, poly-α-olefins having an MFR from 0.1 to about 300 are produced.

In addition to the melt flow rate, the polydispersity index (PI) can vary depending upon various factors and the desired result. The polydispersity index can generally be greater than about 3, such as greater than about 5, and generally less than about 8, such as less than about 6.

The catalysts/methods described above can in some instances lead to the production of poly-α-olefins having bulk densities (BD) of at least about 0.35 cc/g. In another embodiment, poly-α-olefins having a BD of at least about 0.4 cc/g are produced. In another embodiment, poly-α-olefins having a BD of 0.35-0.5 cc/g, or from 0.38-0.46 cc/g are produced.

The catalysts/methods described above can lead to the production of poly-α-olefins having a Span of less than 1.0. In some embodiments, the Span is less than 0.6.

Embodiments of the present invention can lead to the production of a propylene block copolymer and impact copolymers including polypropylene based impact copolymer having one or more excellent melt-flowability, moldability, desirable balance between rigidity and elasticity, good stereospecific control, good control over polymer particle size, shape, size distribution, and molecular weight distribution, and impact strength with a high catalytic efficiency and/or good operability. Employing the catalyst systems containing the solid catalyst component according to embodiments of the present invention yields catalysts simultaneously having high catalytic efficiency, and one or more of excellent melt-flowability, extrudability, moldability, rigidity, elasticity and impact strength.

The following examples illustrate embodiments of the present invention. Unless otherwise indicated in the following examples and elsewhere in the specification and claims, all parts and percentages are by weight, all temperatures are in degrees Celsius, and pressure is at or near atmospheric.

EXAMPLES

Abbreviations and Definitions

"$D_{10}$" represents the size of particles (diameter), wherein 10% of particles are less than that size, "$D_{50}$" represents the size of particles, wherein 50% of particles are less than that size, and "$D_{90}$" represents the size of particles, wherein 90% of particles are less than that size. "Span" represents the distribution of the particle sizes of the particles. The value can be calculated according to the following formula:

$$\text{Span} = (D_{90} - D_{10})/D_{50}$$

"PP" prior to any D or Span value indicates the D value or Span value for polypropylene prepared using the catalysts indicated.

BD is an abbreviation for bulk density, and is reported in units of g/ml.

CE is an abbreviation for catalyst efficiency and is reported in units of Kg polymer per gram of catalyst (Kg/g) during the polymerization for 1 hour.

MFR is an abbreviation for melt flow rate and is reported in units of g/10 min. The MFR is measured cording to ASTM standrs D1238.T The catalyst component particle size analysis was conducted using laser light scattering method by Malvern Mastersizer 3000 instrument. Toluene used as a solvent.

The surface area and pore size distribution of the catalyst components were measured by Micrometrics ASAP 2020 instrument. The catalyst component samples were degassed by heating at 60° C. under vacuum for few hours before the measurement.

The polydispersity index index (PI) and zero shear viscosity for polymer samples were obtained from rheological data by ARES G2 Rheometer. The stabilized polymer sample is pressed on hot press to make plate. The polymer plate is then analyzed on the Rheometer. From the data plot PI and zero shear viscosity are calculated using built in MWD software.

NPDE is an abbreviation for a non-phthalate diaryl ester and can be of the formula:

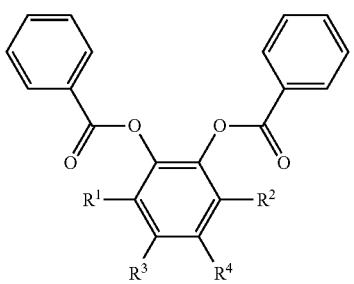

where $R^1$—R4-selected from substituted or unsubstituted aryl groups, $R^3$ $R^4$ $R^5$ $R^6$ are the same or different alkyl or cycloalkyl having 1 to 20 carbon atoms, heteroatom or combination of them. As used herein, NPDE1 is 3-methyl-5-tert-butyl-1,2-phenylene dibenzoate. NPDE2, on the other hand, is described in paragraph 52 of U.S. Patent Publication US 2013/0261273, which is incorporated herein by reference.

SYLTHERM is a tradename for a polydimethyl siloxane (PDMS) that is commercially available from Dow Chemical.

VISCOPLEX is a tradename for a polyalkyl methacrylate available from Evonik.

EB is an abbreviation for ethyl benzoate.

TBP is an abbreviation for tributyl phosphate.

ECH is an abbreviation for epichlorohydrin.

TEOS is an abbreviation for tetraethylorthosilicate.

Ti, Mg, and D are the weight percentages (wt %) for each of the titanium, magnesium, and internal donor (NPDE), respectively, in the composition.

XS is an abbreviation for xylene solubles, and is reported in units of wt %.

Bulk Propylene Polymerization

Where catalysts of the examples are used in a method of propylene polymerization the following method was used. The reactor was baked at 100° C. under nitrogen flow for 30 minutes prior to the polymerization run. The reactor was cooled to 30-35° C. and cocatalyst (1.5 ml of 25 wt % triethylaluminum (TEA1)), C-donor [cyclohexylmethydimethoxysilane](1 ml), hydrogen (3.5 psi) and liquid propylene (1500 ml) were added in this sequence into the reactor. The catalyst (5-10 mg), loaded as a mineral oil slurry, was pushed into the reactors using high pressure nitrogen. The polymerization was performed for one hour at 70° C. After the polymerization, the reactors were cooled to 22° C., vented to atmospheric pressure, and the polymer collected.

Gas Phase Propylene Polymerization

Where catalysts of the examples are used in a method of propylene polymerization the following method was used. The reactor was baked at 100° C. under nitrogen flow for 30 minutes prior to the polymerization run. The reactor was cooled to 30° C. and propylene was charged (120 g), with cocatalyst (0.27 ml of 25 wt % triethylaluminum (TEA1)), C-donor [cyclohexylmethydimethoxysilane](0.38 ml), and hydrogen (0.5 g). A reactor was heated to 35° C. and the catalyst component (0.5-0.7 mg) was flashed to the reactor with propylene (120 g). The polymerization was performed for one hour at 70° C. After the polymerization, the reactors were cooled to 22° C., vented to atmospheric pressure, and the polymer collected.

Examples 1-3 illustrates preparing the catalyst components using an organosilicon compound without supportive donor and provides the properties of polymer produced using a bulk propylene polymerization scheme.

Example 1 demonstrates preparing the catalyst component using tetraethylorthosilicate. The catalyst produced polymer with raspberry shape particle morphology with BD below 0.40 g/cc and B/L3<0.7

3.3 g of $MgCl_2$, 20 g toluene, 6.7 g TBP, 6.43 g of ECH was charged to reactor. The mixture was heated to 60° C. and held for 8 hours at 600 RPM agitation speed. The mixture was allowed to cool to 25°. 27 grams of toluene and 1.5 grams of tetraethylorthosilicate in 3 grams toluene were added to the reactor at 25° C. The reactor was cooled to −25° C. and 65.2 grams of $TiCl_4$ was added. After the addition, the stirring rate was dropped to 200 rpm and the reaction was heated to 35° C. for over two hours and held for 30 minutes, heated to 85° C. for 30 minutes and held for 30 minutes. Filter. The reaction was washed with 50 mL of toluene, 3x. 65 ml of toluene was added and the reactor was heated to 40° C. @400 RPM. 0.64 grams of NPDE1 was added and the reactor was heated up to 105° C. and held for one hour. Filter. 65 mL of 10% $TiCl_4$ was added and the temperature raised to 105° C. for one hour. Filter. 65 mL of 10% $TiCl_4$ was added and the temperature raised to 110° C. for 30 minutes and filtered 3 times. The solid was washed with 50 mL of hexanes @65° C. and 400 RPM 3 times. The catalyst component was discharged as a hexane slurry. The analytical data and the catalyst performance is presented below.

Example 2 demonstrates the catalyst component using two organosilicon compounds (tetraethylorthosilicate and Syltherm PDMS) and $Al(OiPr)_3$. The internal donor was added in two places: in before the solid formed and to the solid component. The catalyst produced polymer with rounded raspberry type morphology and improved bulk density (BD=0.44 g/cc).

3.3 g of $MgCl_2$ to correct subsript, 0.25 g Al(O-iPr)3, 20 g toluene, 9.1 g TBP, 1.0 g Syltherm(PDMS), 3.55 g of ECH was charged to reactor. The mixture was heated to 60° C. and held for 8 hours at 600 RPM agitation speed. The mixture was allowed to cool to 25° C. 27 grams of toluene, 1.5 grams of TEOS in 3 grams of toluene, and 0.64 grams of NPDE1were added the reactor. The reactor was chilled to −25° C. and 65.4 grams of $TiCl_4$ was added to the reactor. The agitation was set to 300 RPM and ramped to 35° C. over 2 hours. The reaction was held at 35° C. for 30 minutes @300 RPM. The reaction was heated to 85° C. and held for 30 minutes. The reaction was filtered and 50 mL of toluene was added. The reactor was heated to 40° C. @400 RPM and 0.64 grams of NPDE1 was added. The reactor continued heating to 105° C. and was held for 1 hour, then allowed to settle and decanted. 65 mL of 10% $TiCl_4$ was added, heated to 105° C. and held for 1 hour. The reaction was allowed to settle and it was decanted. 65 mL of 10% $TiCl_4$ was added, heated to 110° C. and held for 1 hour. The reaction was allowed to settle and it was decanted. 50 mL of hexane was added and stirred for 5 minutes @jacket temperature of 65° C. The reaction was allowed to settle and was decanted. Hexane was then added and the product was discharged as a hexane slurry.

Example 3 demonstrates the catalyst component using two organosilicon compounds (tetraethylorthosilicate and Syltherm PDMS) and Al(OiPr)3. The internal donor was added to the solid component. The particle size of catalyst component increased to 14 microns (compared with examples 1 and 2).

3.3 g of $MgCl_2$, 0.25 g Al(O-iPr)3, 20 g toluene, 6.7 g TBP, 1.0 g Syltherm(PDMS), 6.43 g of ECH was charged to the reactor. The mixture was heated to 60° C. and held for 8 hours @600 RPM agitation speed. The mixture was allowed to cool to 25° C. 27 grams of toluene, 1.5 grams of TEOS in 3 grams of toluene were added to reactor at 600 rpm and 25° C. The reactor was cooled to −25° C. and 65.2 grams of TiCl$_4$ was added. The reactor was heated to 35° C. @200 RPM for over two hours and held at 35° C. for 30 minutes; heated to 85° C. over 30 minutes and held at 85° C. for 30 minutes and decanted washed 3x with toluene. Cool to 25° C. and let sit over weekend. Filter, add 65 mL of toluene. Heat to 40° C. @400 RPM and add 0.64 grams NPDE1. Heat to 105° C. for one hour. Filter. Add 65 mL of 10% TiCl$_4$, heat to 105° C., hold for one hour. Filter. Add 65 mL of 10% TiCl$_4$, heat to 110° C., hold for one hour. Filter. Wash with 50 mL of hexanes 3x, jacket temperature @65, agitate 5 minutes between washes. Discharge as hexane slurry.

Example 4 (Comparative). This example demonstrates preparing the catalyst component without organosilicon compound. The catalyst produced polymer with irregular morphology with agglomerated polymer particles.

3.3 g of MgCl$_2$, 1.15 g Al(O-iPr)3, 20 g toluene, 6.7 g TBP, 6.43 g of ECH was charged to reactor 14A. The mixture was heated to 60° C. and held for 8 hours @600 RPM agitation speed. The mixture was allowed to cool to 25° C. 30 grams of toluene was added to the reactor at 25° C. and 600 RPM. The reactor was cooled to −25° C. and 65.2 grams of TiCl$_4$ was added. After the addition, the stirring rate was dropped to 200 and the reaction was heated to 35° C. over two hours. Hold for 30 minutes. Heated to 85° C. for 30 minutes. Hold for 30 minutes. Filter. The reaction was washed with 50 mL of toluene, 3x, JT 80° C., 400 RPM. Filter. 65 ml of toluene was added and the reactor was heated to 40° C. @400 RPM. 0.64 grams NPDE1 was added and the reactor was heated up to 105° C. and held for one hour. Filter. 65 mL of 10% TiCl$_4$ was added and the temperature raised to 105° C. for one hour. Filter. 65 mL of 10% TiCl$_4$ was added and the temperature raised to 110° C. for 30 minutes and filtered 3 times. The reactor was washed with 50 mL of hexanes @65° C. and 400 RPM 3 times. The product was discharged as a hexane slurry.

TABLE 1

Catalyst components prepared with two organosilicon compounds and Al(OiPr)3

| Example | Component Present | D10 | D50 | D90 | Span | Ti % | Mg % | NPDE1 % |
|---|---|---|---|---|---|---|---|---|
| Example 1 | TEOS | 5.81 | 9.84 | 14.9 | 0.928 | 3.79 | 17.34 | 9.83 |
| Example 2 | Al(OiPr)3, Syltherm, TEOS, NPDE1 | 5.02 | 8.94 | 13.8 | 0.982 | 3.94 | 15.76 | 17.08 |
| Example 3. | Al(OiPr)3, Syltherm, TEOS, | 9.67 | 14.5 | 21.5 | 0.817 | 4.19 | 17.64 | 9.73 |
| Example 4 (comparative) | Al-O only | 3.85 | 7.12 | 13.5 | 1.356 | 2.818 | 18.48 | 7.41 |

TABLE 2

Catalysts and polymer properties (catalyst components prepared with two organosilicon compounds and Al(OiPr)3)

| Catalyst component | CE kg/g | MFR, g/10 min | XS, % | BD, g/cc | PP D10 | PP D50 | PP D90 | PP Span | B/L3 | Comment on PP morphology |
|---|---|---|---|---|---|---|---|---|---|---|
| Example 1 | 65 | 1.46 | 3.1 | 0.397 | 353 | 590 | 1120 | 1.3 | 0.66 | Raspberry shape |
| Example 2 | 91.2 | 0.25 | 1.88 | 0.443 | 319 | 495 | 915 | 1.204 | 0.681 | Rounded raspberry shape |
| Example 3 | 54.4 | 1.84 | 2.22 | 0.394 | 319 | 617 | 1081 | 1.235 | 0.682 | Grape shape |
| Example 4 (comparative) | 51.4 | 2.86 | 4.07 | 0.237 | 612 | 1393 | 2085 | 1.057 | 0.624 | Irregular morphology |

Examples 5-13 illustrate preparing the catalyst components using a supportive donor, ethyl benzoate. (EB)

TABLE 3

Catalyst components prepared with organosilicon compounds and with supportive donors

| Example | Comments | D10 (μ) | D50 (μ) | D90 (μ) | Span | Ti % | Mg % | NPDE1, % |
|---|---|---|---|---|---|---|---|---|
| Example 5 (Comparative) | No epoxy compound | 6.0 | 10.5 | 18.3 | 1.173 | 3.6 | 16.16 | 16.17 |
| Example 6 | Syltherm/TEOS = 2/1; EB/MgCl$_2$ = 0.34 | 14.9 | 24.0 | 37.2 | 0.929 | 3.36 | 17.62 | 13.5 |
| Example 7 | Syltherm/TEOS = 1/1; EB/MgCl$_2$ = 0.34 | 9.4 | 18.0 | 26.6 | 0.960 | 3.26 | 15.21 | 11.7 |

TABLE 3-continued

Catalyst components prepared with organosilicon compounds and with supportive donors

| Example | Comments | D10 (μ) | D50 (μ) | D90 (μ) | Span | Ti % | Mg % | NPDE1, % |
|---|---|---|---|---|---|---|---|---|
| Example 8 | TEOS; EB/MgCl$_2$ = 0.34 | 12.7 | 18.6 | 26.1 | 0.720 | 3.71 | 16.37 | 14.2 |
| Example 9 (19724-17) | Syltherm/TEOS = 1/2; EB/MgCl$_2$ = 0.34 | 8.7 | 14.1 | 19.8 | 0.788 | 3.53 | 16.25 | 11.7 |
| Example 10 19724-14 | Syltherm; EB/MgCl$_2$ = 0.34 | 3.1 | 10.5 | 17.2 | 1.338 | 2.96 | 16.4 | 11.3 |
| Example 11 (19724-67) batch 4 | TEOS; EB/MgCl$_2$ = 0.26, rpm 300 | 6.4 | 10.2 | 14.9 | 0.842 | 3.16 | 17.36 | 10.4 |
| Example 12 | TEOS; EB/MgCl$_2$ = 0.26, rpm 200 | 8.6 | 13.6 | 20.7 | 0.889 | 3.01 | 18.56 | 10.9 |
| Example 13 | No organosilicon compound, EB | 6.9 | 11.9 | 18.8 | 0.996 | 3.06 | 17.19 | 11.1 |
| Example 14 (Comparative) | No organosilicon compound, Phthalic anhydride | 9.8 | 20.2 | 33.5 | 1.173 | 2.52 | 18.70 | 10.46 |

TABLE 4

Catalysts and polymer properties (catalyst components prepared with organosilicon compounds and with supportive donors) (bulk propylene polymerization)

| Catalyst Component | CE kg/g | MFR, g/10 min | XS, % | BD, g/ml | PP D50 (μ) | PP Span | B/L3 | PP morphology |
|---|---|---|---|---|---|---|---|---|
| Example 5 (Comparative) | 70.9 | 0.23 | 2.89 | 0.321 | 449 | 1.178 | 0.672 | Irregular, agglomerated small particles |
| Example 6 | 91.7 | 0.10 | 2.29 | 0.383 | 1087 | 0.573 | 0.706 | Rounded raspberry shape |
| Example 7 | 82.9 | 0.26 | 2.28 | 0.418 | 836 | 0.435 | 0.720 | Rounded raspberry shape |
| Example 8 | 81.1 | 0.17 | 2.40 | 0.424 | 899 | 0.433 | 0.738 | Rounded shape |
| Example 9 | 84.3 | 0.17 | 3.14 | 0.454 | 705 | 0.704 | 0.707 | Rounded raspberry shape |
| Example 10 | 83.1 | 0.12 | 2.23 | 0 421 | 970 | 0.992 | 0.625 | Raspberry shape |
| Example 11 | 81.9 | 0.34 | 2.44 | 0.447 | 492 | 0.754 | 0.719 | Rounded shape |
| Example 12 | 79.4 | 0.2 | 2.00 | 0.425 | 643 | 0.736 | 0.713 | Rounded raspberry shape |
| Example 13 (Comparative) | 75.4 | 0.07 | 1.83 | 0.410 | 644 | 0.626 | 0.699 | Grape shape with small subparticles |
| Example 14 (Comparative) | 53.9 | 0.10 | 0.127 | 0.404 | 772 | 0.764 | — | Grape type |

Example 5 (Comparative). The catalyst component was made using tetraethylorthosilicate and the supportive donor, ethyl benzoate, and without an epoxy compound to dissolve MgCl$_2$. This example demonstrates an irregular polymer morphology with low BD.

MgCl$_2$ (12.0 g) and hexane (130 g) were combined to form an initial reaction mixture. To the mixture was then added 2-ethylhexanol (50 g) with stirring (600 rpm), and the temperature was then raised to 120° C. This temperature was then maintained for 4 hours. To the reaction mixture was then added tetraethylorthosilicate (1.75 g in 2.0 g of hexane), and the reaction was held for 20 minutes, followed by cooling to −25° C. At the low temperature, TiCl$_4$ (150 ml) was added over 1.5 hours, after which time the temperature was raised to room temperature. At room temperature ethyl benzoate (2 g in 2 g hexane) was added and the mixture heated to 100° C. A NPDE1 (3.0 g in 5 g of toluene) was then added and the reaction mixture maintained at 100° C. for 1 hour. The solid material was then collected by filtration and it was washed with toluene (3x 200 mL at 85° C. with 10 minute stirrings at temperature before re-filtration). Upon re-suspending the solid in toluene, additional NPDE1 (2.0 g in 5.0 g of toluene) was added at 40° C., and the solid collected by filtration and washed with hexane. The process of adding NPDE1, heating at 110° C. (0.5 hours) and filtering was then repeated process of washing with hexane and filtering was then repeated 3 times. Finally, the solid product was washed with (4×300 ml hexane at 65° C.), and the solid discharged to a hexane slurry.

FIG. 1 is a photograph of the polymer obtained from Example 5 (Comparative). The images presented are SEM images of polypropylene particles produced with the catalysts from the corresponding examples. Because the polymer particles replicate the catalyst particles, we can compare the catalyst morphology in each example. The catalyst and polymer morphology are key factors to consider in commercial polymer production processes. The polymerization processes require good flowability of the polymer for transfer of the polymer from one reactor unit to another. The process should operate without producing any polymer fines that result in a plugging polymerization reactor. Therefore, for any polymerization process the strong and uniform morphology of the catalyst and high bulk density of polymer is preferred.

As illustrated in FIG. 1, the polymer morphology of polymer prepared by Example 5 (Comparative) includes small sub-particles. The bulk density of polymer is very low at 0.321 g/ml. The catalyst and polymer from this example are not favored and would result in the plugging reactor by the fines that are generated.

Example 6. Granular supported catalyst component prepared with Syltherm and TEOS (as organosilicon compounds) and ethyl benzoate as supportive electron donor. The example demonstrates improvement of the catalyst component with larger particle size 24 microns and high activity catalyst (catalyst efficiency 92 kg/g) and producing polymer with rounded shape.

$MgCl_2$ (13.2 g), Al(OCH(CH3)2)3 (1.0 g), toluene (59.5 g), tri-n-butylphosphate (36.3 g), epichlorohydrin (14.25 g), and Syltherm (6.0 g) are combined and heated to 60° C. with agitation at 600 rpm for 8 hours under a nitrogen atmosphere. Upon cooling to room temperature, toluene (140 g) was added, along with ethyl benzoate (4.5 g) and tetraethylorthosilicate (3 g). The mixture was then cooled to −25° C. and $TiCl_4$ (261 g) was slowly added under 600 rpm stirring, while maintaining the temperature at −25° C. After the addition was complete, the temperature was maintained for 1 hour prior to warming to 35° C. over 30 minutes, at which temperature it was held for 30 minutes, then the temperature was raised to 85° C. over 30 minutes, and held for 30 minutes prior to collection of a solid precipitate via filtration. The solid precipitate was washed three times with toluene (200 ml, each wash).

Figure 2:
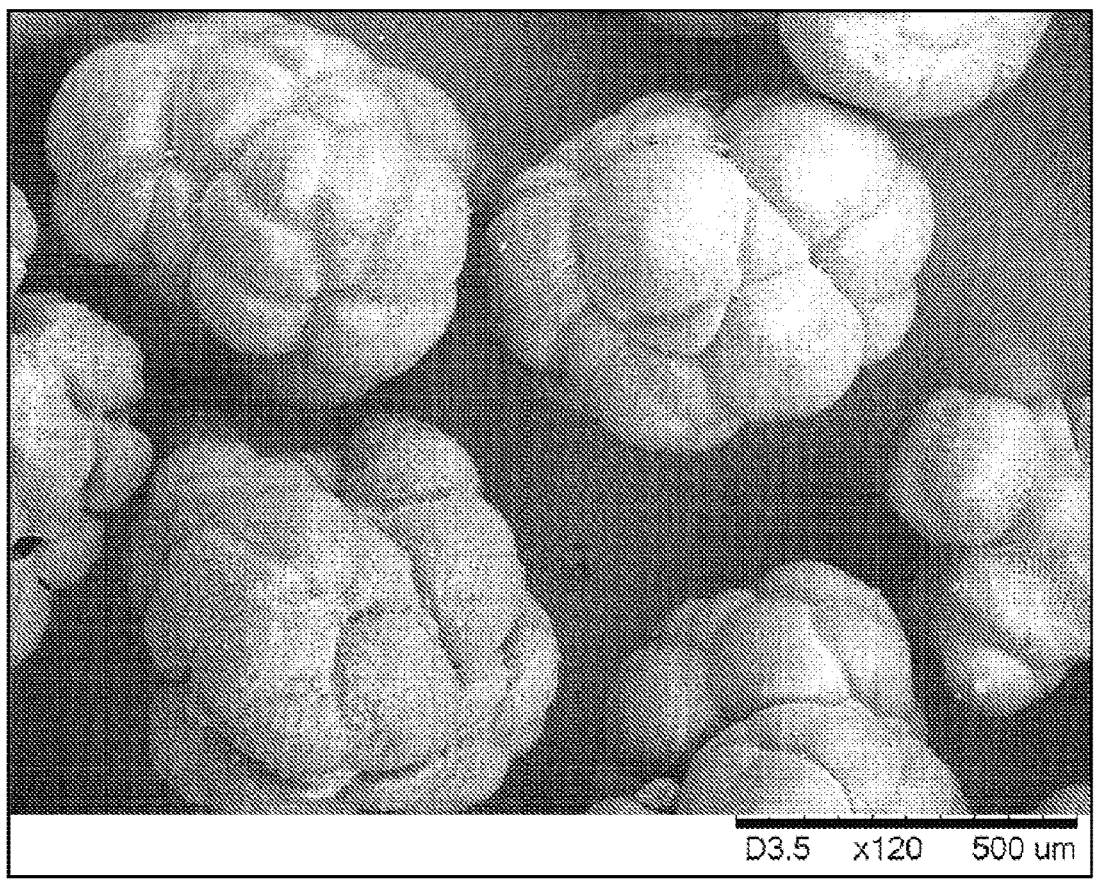
FIG. 2 shows a microscopic view of the polymer produced with the catalyst component of Example 7.

The resulting precipitate was then combined with $TiCl_4$ in toluene (264 ml; 10 vol %). This mixture was heated under agitation to 85° C., followed by addition of NPDE 1 (2.0 g) in toluene (10 g). Heating at 85° C. was continued for 1 hour prior to collection of the solid via filtration. This process of combining with $TiCl_4$ in toluene, heating, adding NPDE 1, was repeated at 95° C. and again at 110° C. before washing the final product four times with hexane (200 ml, each wash), and agitating at 60-65° C. for 10 minutes for each wash. The catalyst component was then discharged as a hexane slurry. FIG. 2 is a photograph of the polymer produced with the catalyst component obtained from Example 6. Polymer morphology like rounded raspberry shape with large subparticles.

Example 7. This example produced a granular supported catalyst illustrating high BD catalyst/PP, with a narrow Span. Example 6 was repeated, however the PDMS was added at 3.0 g, and Al(OCH(CH3)2)3 (0.5 g) and NPDE 1 (2.0 g) was added in toluene wash before the final $TiCl_4$/Toluene treatment.

Example 8. Example 7 was repeated, however the TEOS was added at 6.0 g and no Syltherm was added. This example produced a granular supported catalyst which produced polymer with rounded shape morphology (B/L3=0.74)

Example 9. This example produced a granular supported catalyst illustrating improvement of the catalyst and polymer morphology, and showing high BD catalyst/PP, with a narrow Span. Example 7 was repeated; however the TEOS was added at 1.50 g.

Example 10. Illustrates preparation of catalyst component using Syltherm as organosilicon silicon compound. Granular supported catalyst component demonstrating reduction of particle sizes. Example 7 was repeated, however no TEOS was added.

Figure 3:
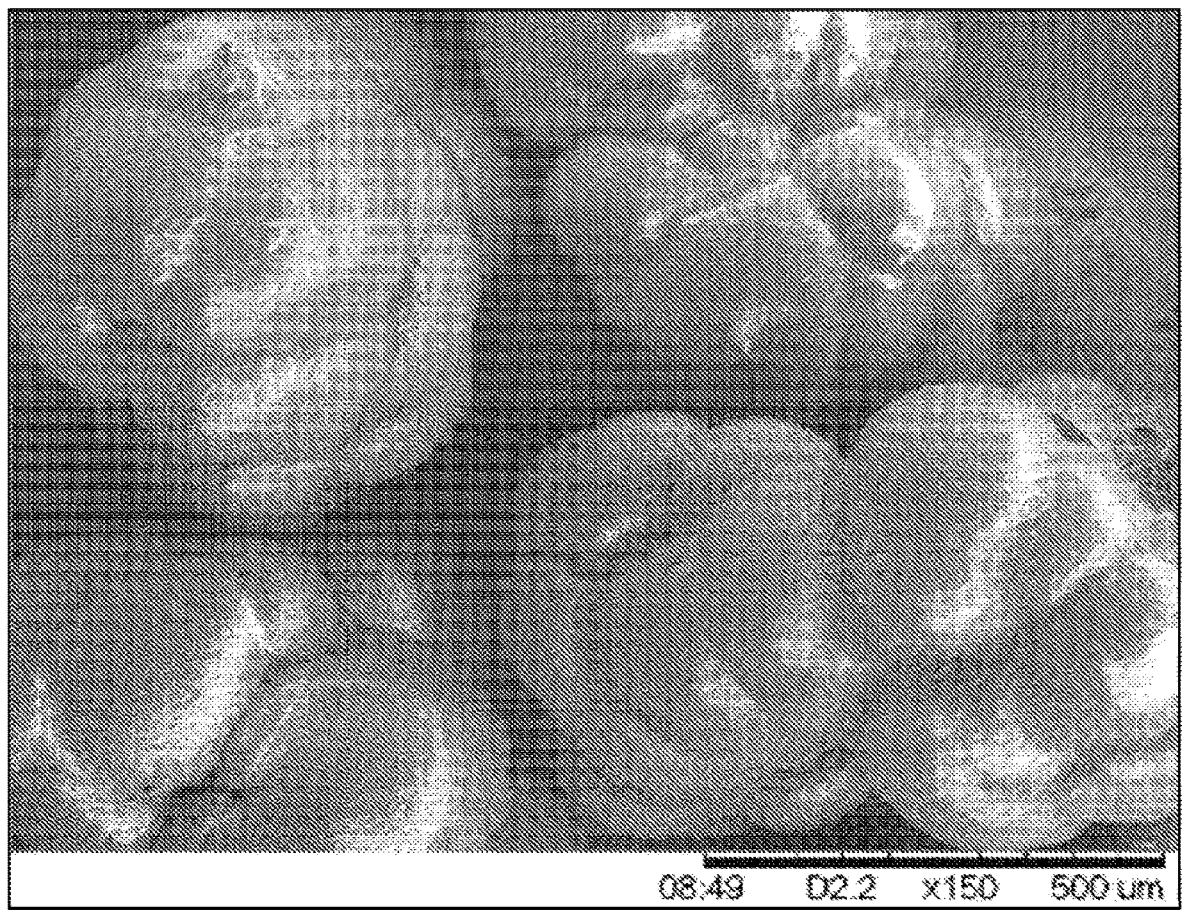
FIG. 3 shows a microscopic view of the polymer produced with the catalyst component of Example 9.

FIGS. 2 and 3 illustrate the rounded raspberry type morphology of polymers prepared by the catalysts of Examples 7, and 9, respectively, using an epoxy compound to dissolve $MgCl_2$, along with varying combinations of organosilicon compounds (polydimethoxysilane (PDMS) and tetraethoxysilane (TEOS)), and ethyl benzoate, demonstrate improvement in catalyst and polymer morphology. The FIGS. 2 and 3. show the materials as having a well-defined morphology. The large sub-particles are associated in large particles. The polymers produced with these catalysts exhibit a high density (>0.40 g/ml) and sphericity (B/L3>0.71) (see tables above).

Example 11. Demonstrates effect of amount of supportive donor on catalyst component particle size. Example 8 was repeated except amount of ethyl benzoate was reduced from 0.34 g/gMgCl$_2$ to 0.26 g/gMgCl$_2$ which resulted in a reduction of the catalyst component particle size from 18.6 microns to 10.2 microns.

Figure 4:
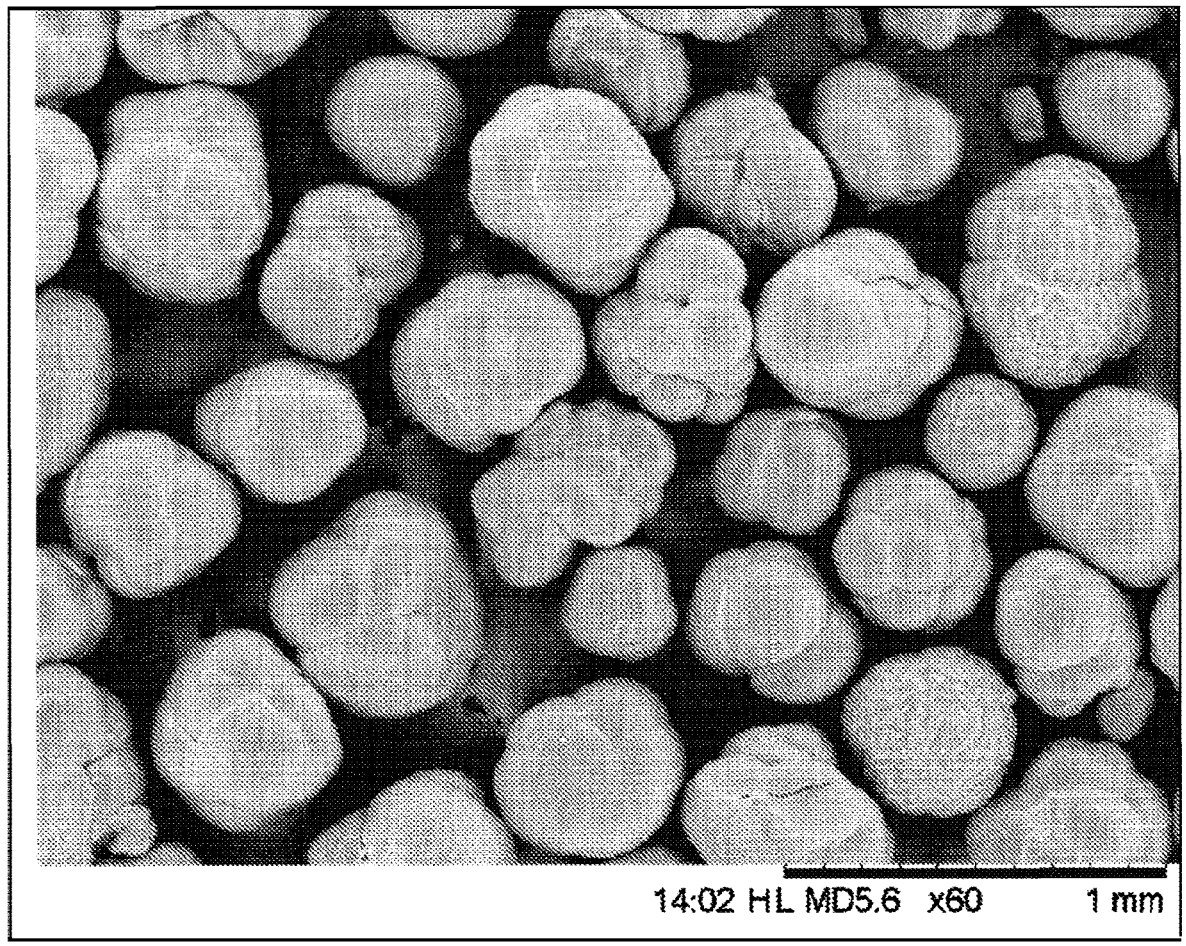
FIG. 4 shows a microscopic view of the polymer produced with the catalyst component of Example 11.

FIG. 4 the rounded shape of polymer morphology produced by the catalyst from Example 11.

Figure 5:
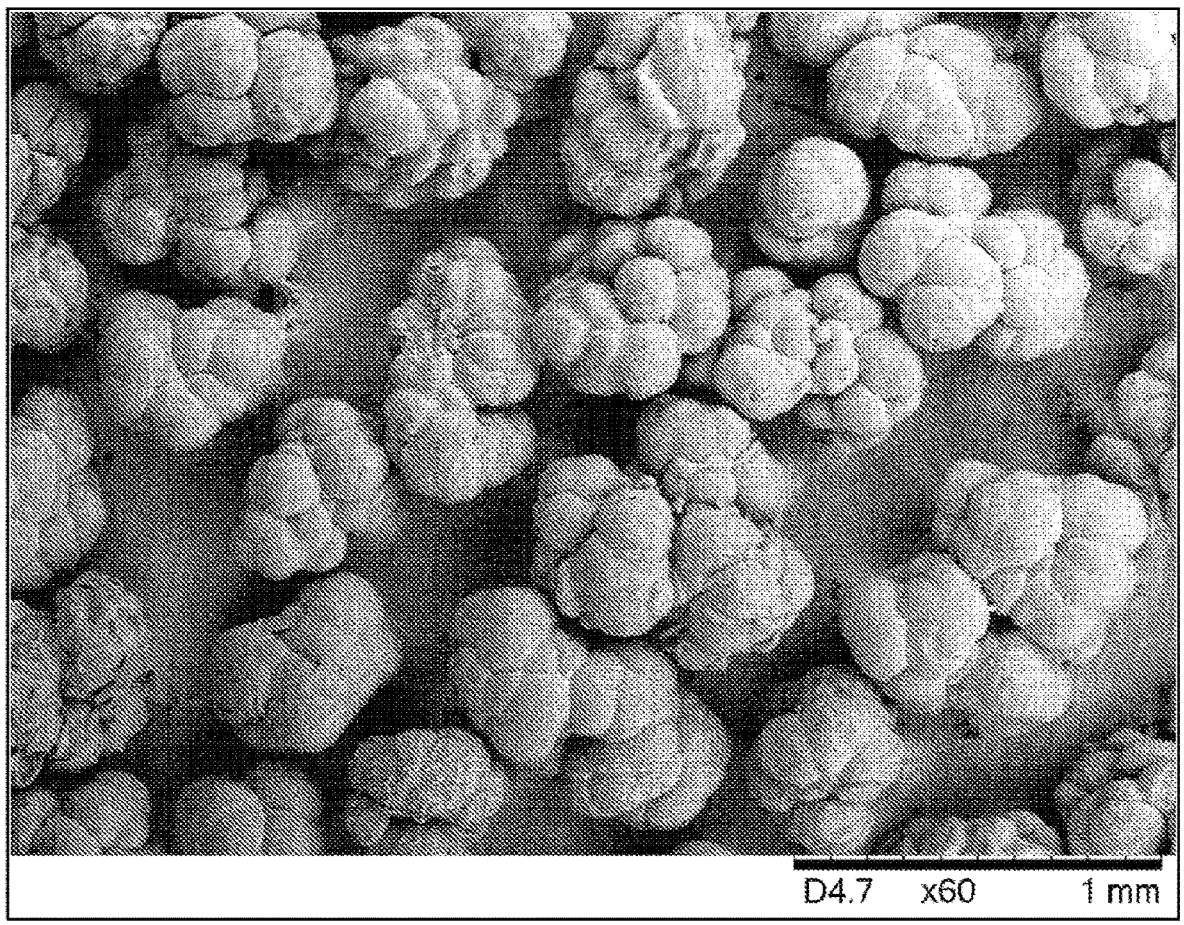
FIG. 5 shows a microscopic view of the polymer produced with the catalyst component of Example 13 (Comparative).

Example 12. Demonstrates effect of agitation speed during the precipitation of the catalyst component on catalyst component particle size. Example 11 was repeated except the agitation speed was reduced from 300 rpm to 200 rpm, which resulted in increasing catalyst component particle size from 10.2 microns to 13.6 microns Example 13. (Comparative). Granular supported catalyst demonstrating reduction of particle sizes and bulk density of the catalyst and polymer. No Al(OCH(CH3)2)3, Syltherm, or TEOS was used. Example 7 was repeated, however no Al(OCH(CH3)2)3, PDMS, or TEOS was added. Example 13 demonstrates that performance of the catalyst component prepared by using an epoxy compound to dissolve the $MgCl_2$, and using only ethyl benzoate as a supportive donor without using organosilicon compounds. FIG. 5 represents the morphology of polymer produced according to Example 13. Each polymer particle contains numerous small subparticles. In some polymerization processes, this morphology is not favored because these particles can be easily disintegrated up during the polymerization process.

Example 14. (Comparative). Catalyst component made with phthalic anhydride as a precipitation agent. The catalyst component contains bis(1,3-dichloro-iso-propyl) phthalate (1.2%) and phthaloyl chloride (0.3%) as a reaction product of phthalic anhydride with $TiCl_4$ and Mg-compounds during the catalyst component preparation. The catalyst component shows lower catalyst activity than the catalyst produced under the current claims. The polymer particle morphology is a grape type with B/L3<0.70.

$MgCl_2$ (13.2 g), toluene (190.0 g), tri-n-butylphosphate 26.6 g), ECH (25.6 g) were combined and heated to 60° C. with agitation at 600 rpm for 8 hours under a nitrogen atmosphere. Phthalic anhydride was added (4.6 g) at 60° C. The mixture was then cooled to −25° C., at which temperature $TiCl_4$ (260 g) was slowly added with 600 rpm agitation. The temperature was maintained for 1 hour, followed by raising the temperature to 10° C. over 30 minutes, holding for 30 minutes, raising to 85° C. over 70 minutes, and holding for 15 minutes before collecting the solid via filtration. The solid was washed three times with toluene (200 ml) for 10 minutes each at the 85° C. The solid was then collected by filtration and washed with toluene (265 ml). After filtration, the $TiCl_4$/toluene solution and NPDE 1 (3.0 g) in toluene (2 g), was added and heated at 105° C. After again filtering, the solid was collected, and washed with the $TiCl_4$/toluene solution at 110° C. under agitation. Finally, the solid was washed with hexane (200 ml) four times under agitation at 60-65° C., with the catalyst being discharged as a hexane slurry. The catalyst of Example 14 demonstrates lower catalyst activity than the catalyst prepared without phthalic anhydride.

Examples 15-17 illustrate the catalyst component preparation using TEOS as organosilicon compound and ethyl benzoate as a supportive electron donor. Examples 18-23 illustrate the polymerization data in bulk propylene and gas phase reactors producing polymer with substantially spherical shape.

Example 15. Example of 11 was repeated in a scale of $MgCl_2$=20 kg

Example 16. Add 13.2 g $MgCl_2$, 0.5 g Al(OR)3, 72 g toluene, 25.7 g ECH, 26.8 g TBP, Heat and Agitate at 60C/600 rpm/8 hr. Cool down to 25 C. Leave for next day under N2 Blanket. Add 75.0 g toluene, 3.5 g EB in 12 g toluene, 6.0 g TEOS in 8 g toluene @25C. Cool to −25C @600 rpm and add 260.8 g $TiCl_4$ slowly addition. Raise from −25C to 35C over 2 hr @350 rpm and hold at 35C for 30 min/350 rpm.Raise from 35C to 85C in 30 min and hold at 85C for 30 min @350 rpm filter. Wash w/200 ml toluene/3×/10 min & add 200 ml toluene leave under N2 Blanket Next day of Toluene heat, add 1.25 g of NPDE1, heat 105° C. 400rpml hr. Filter, 1st Act add 265 ml 10% h $TiCl_4$/tol heat to 105C/400 rpm/1 hr and filter From the 2nd Act to 4th Act, add 265 ml 10% $TiCl_4$/tol heat to 110C/400 rpm/30 minutes and filter Wash w/200 ml of hexane @65C JT/4X/10 min & discharge as hexane slurry Example 17. Example 15 was repeated with increasing the NPDE1 amount by 10%

Figure 6:
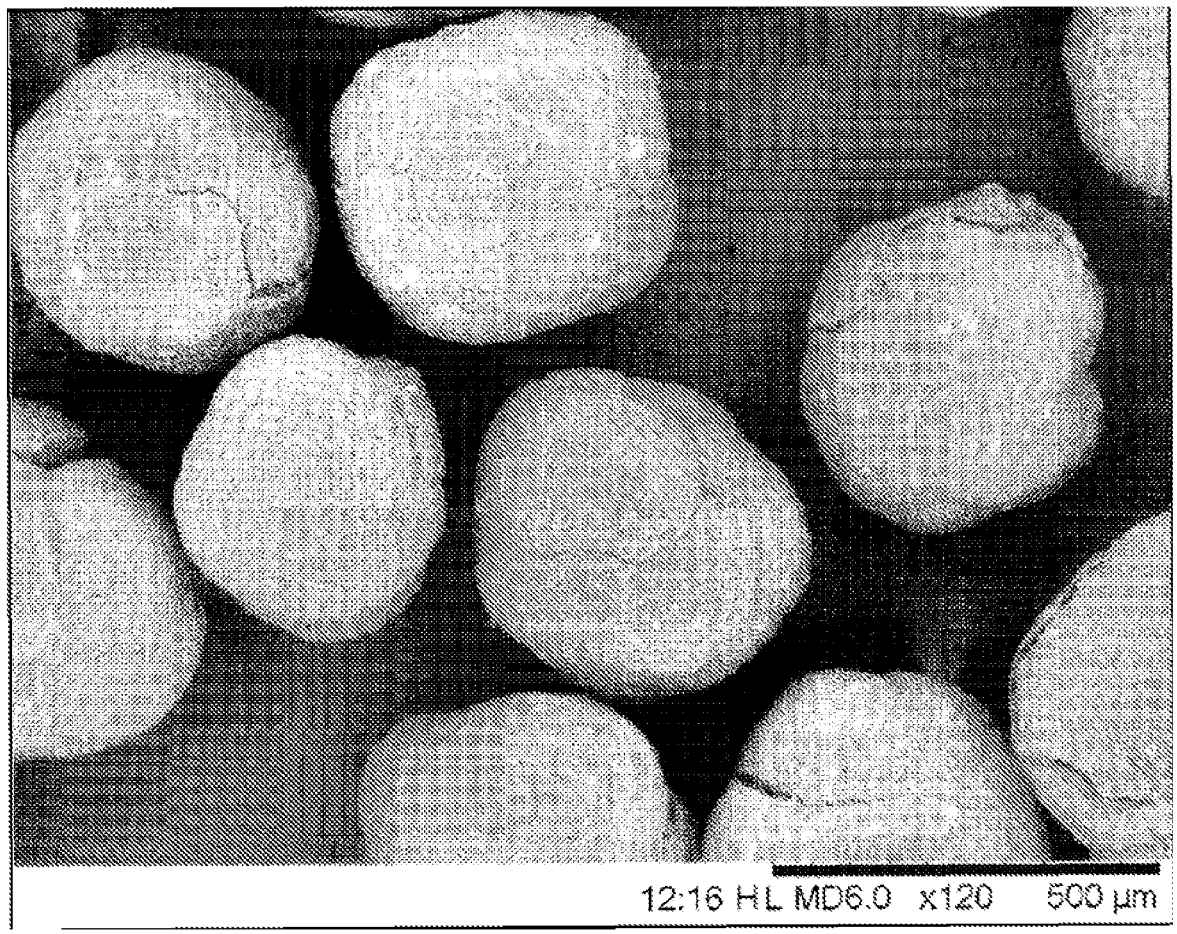
FIG. 6 shows a microscopic view of the polymer produced with the catalyst component of Example 23.

Examples 18-23 demonstrate production polymer in bulk and gas phase polymerization reactors with substantially spherical shape of particles with B/L3 of 0.8. FIG. 6 shows PP with substantially spherical shape morphology from example 23.

Surface area (BET) measurement and porosity of the catalyst components show surface area of around 400 m2/g.

TABLE 7

| | Surface area (BET) | | | | |
|---|---|---|---|---|---|
| | Catalyst component | | | | |
| | SA. BET.m²/g | Ads PV. cm²/g | Des PV. cm²/g | Ads PD. A | Des PD. A |
| Example 27 | 395.0 | 0.2714 | 0.2719 | 27.4841 | 27.5313 |

Examples 24-27 illustrate the relationship of the catalyst performances and relatively ratio of supportive electron donor and internal electron donor. The catalyst isotacticity reduces (% XS) with increasing EB/NPDE1 ratio but the catalyst activity does not change sufficiently.

TABLE 5

| | Catalyst Component | Comment | D10 | D50 | D90 | Span | Ti % | Mg % | NPDE1% |
|---|---|---|---|---|---|---|---|---|---|
| Example 15 | TEOS, EB | (20 kg of $MeCl_2$ scale) | 8.8 | 11.6 | 15.4 | 0.570 | 3.04 | 16.85 | 10.68 |
| Example 16 | ECH/$MgCl_2$ = 2 (mol); | TEOS, EB | 11.5 | 17.5 | 26.4 | 0.851 | 2.95 | 16.88 | 10.54 |
| Example 17 | TEOS, EB | (20 kg of $MgCl_2$ scale) | 6.19 | 11.4 | 18.1 | 1.044 | 2.56 | 16.64 | 10.37 |

TABLE 6

| Example | Catalyst Component | Polymerization condition | CE kg/g | MFR g/10 min | XS, % | BD, g/cc | PP D10 | PP D50 | PP D90 | PP Span | B/L3 | PP morphology |
|---|---|---|---|---|---|---|---|---|---|---|---|---|
| Example 18 | From example 15 | Bulk | 70.6 | 1.36 | 2.40 | 0.463 | 490 | 717 | 1698 | 1.685 | 0.706 | Rounded shape |
| Example 19 | From example 15 | Gas Phase | 64.3 | 4.20 | 2.15 | 0.436 | 443 | 511 | 672 | 0.447 | 0.797 | Substantially spherical shape |
| Example 20 | From example 16 | Bulk | 93.6 | 0.26 | 2.25 | 0.432 | 706 | 848 | 1107 | 0.473 | 0.762 | Rounded Shape |
| Example 21 | From example 16 | Gas Phase | 63.9 | 1.70 | 1.94 | 0.389 | 645 | 756 | 919 | 0.363 | 0.782 | Substantially spherical shape |
| Example 22 | Front example 17 | Bulk | 90.1 | 0.33 | 2.04 | 0.435 | 446 | 558 | 843 | 0.711 | 0.763 | Substantially spherical shape |
| Example 23 | From example 17 | Gas Phase | 60.6 | 1.4 | 1.89 | 0.414 | 423 | 508 | 716 | 0.575 | 0.763 | Substantially spherical shape |

TABLE 8

Analytical data for catalyst components and corresponding catalyst polymerization data with variable ratio of supportive electron donor and electron donor

| Example | NPDE1/ MgCl2, wt | Ti, % | Mg % | NPDE1, % | EB, % | CE kg/g | MFR, g/10min | XS, % |
|---|---|---|---|---|---|---|---|---|
| Example 24 | 0.227 | 3.37 | 18.62 | 13.06 | 6.03 | 102.3 | 0.16 | 2.21 |
| Example 25 | 0.182 | 3.37 | 16.93 | 10.70 | 7.46 | 93.7 | 0.14 | 2.53 |
| Example 26 | 0.152 | 3.57 | 17.15 | 9.34 | 8.50 | 91.6 | 0.35 | 3.07 |
| Example 27 | 0.121 | 3.62 | 16.7 | 7.73 | 9.90 | 96.3 | 0.35 | 3.87 |

Catalyst components in Examples 24 through 27 were produced as in Example 8 except the amount of NPDE1 was used as in Table 8. Catalyst component particle sizes are 32 microns (produced with agitation speed of 200 rpm during the support precipitation).

Example 28 illustrates granular catalyst components prepared with NPDE2 as an internal donor diaryl ester and example 29 presents polymerization data in bulk propylene.

Example 28. Example 8 was repeated except NPDE2 was used as internal electron donor (NPDE2/MgCl$_2$=0.18 (wt)

The catalyst component was tested in bulk propylene polymerization to evaluate the hydrogen response on MFR.

TABLE 8

Analytical data for catalyst components with NPDE 2

| | Conditions | D10 | D50 | D90 | Span | Ti % | Mg % | D % |
|---|---|---|---|---|---|---|---|---|
| Example 28 | NPDE2, TEOS | 11.2 | 18.8 | 28.9 | 0.940 | 3.53 | 17.12 | n/a |

TABLE 9

Polymerization data using catalyst component from example 28

| | Catalyst component | 112, SL | CE kg/g | MFR, g/10 min | XS, % | BD, g/cc | PP D10 | PP D50 | PP D90 | PP Span | B/L3 |
|---|---|---|---|---|---|---|---|---|---|---|---|
| Example 29 | From example 28 | 5 | 94.7 | 1.5 | 3.36 | 0.424 | 762 | 986 | 1604 | 0.854 | 0.696 |

As shown above, Example 29 was conducted at a hydrogen concentration of 5 SL. In general, the hydrogen concentration can be from about 5 SL to about to 40 SL or higher. In general, at lower hydrogen concentrations, such as less than about 20 SL, such as less than about 10 SL, polymers are produced having a relatively low melt flow rate. For instance, the melt flow rate can be less than about 8 g/10 min, such as less than about 5 g/10 min, such as less than about 3 g/10 min, such as less than about 2 g/10 min, such as less than 1 g/10 min, and generally greater than about 0.01 g/10 min. At higher hydrogen amounts, such as greater than about 30 SL, such as from about 30 SL to about 50 SL, the melt flow rate can be dramatically increased. For instance, the melt flow rate can be greater than about 100 g/10 min, such as greater than about 150 g/10 min, such as greater than about 200 g/10 min, such as greater than about 250 g/10 min, such as greater than about 300 g/10 min, such as greater than about 350 g/10 min, such as greater than about 400 g/10 min, such as greater than about 450 g/10 min, such as greater than about 500 g/10 min, and generally less than about 800 g/10 min.

Hydrogen concentration can have some impact on catalyst activity. In general, the catalyst activity can range from about 90 kg/g to about 200 kg/g. A catalyst activity of from about 150 kg/g to about 200 kg/g can reflect a flat kinetic profile.

Hydrogen concentration generally does not impact bulk density or particle size. For instance, the bulk density can be greater than about 0.3 g/cc, such as greater than about 0.35 g/cc, such as greater than about 0.4 g/cc, and generally less than about 0.5 g/cc, such as less than about 0.45 g/cc. The D50 particle size can generally be from about 500 microns to about 1700 microns, and generally from about 800 microns to about 1400 microns. The B/L3 of the polymer can generally be greater than about 0.6, such as greater than about 0.65 and generally less than about 0.8, such as less than about 0.75.

Examples 30-32 illustrate preparing the catalyst components using 1,3 diether (3,3-bis(methoxymethyl)-2,6-dimethylheptane) (DEMH) as an internal donor.

Example 30 Added 6.6 g MgCl$_2$, 0.5 g Al(O-iPr)3, 48 g toluene, 18.2 g TBP, 7.1 g ECH to reactor. Heated and agitated at 60° C./600 rpm/8 hr. Cooled down to 25C. Added 35 g toluene, 2.25 g ethyl benzoate in 5 g toluene, 3.0 g TEOS in 5 g toluene and 0.75 g of DEMH in 5 g of toluene @25C. Cooled to −25C @600 rpm and added 130.4 g TiCl$_4$ slowly addition. Raised from −25C to 35C over 2 hr @250 rpm and held at 35C for 30 min/250 rpm. Raised from 35C to 85C in 30 min, held for 1 hour and filtered off. Washed w/100 ml toluene/3×/10 min. Added 132 ml of 10% TiCl$_4$/toluene, added (1.25 g of DEMH in 5 g of toluene @40C. heat at 80 C for 1 h, filtered off. Added 132 ml of 10% TiCl$_4$/tol and heated at 105 for 1 hour. The treatment was repeated at 110° C. for 30 min three more times. The solid was washed with hexane and discharged as a hexane slurry.

Example 31. Example 8 was repeated except the solid precipitation was conducted at 350 rpm agitator speed and 0.80 g of DEMH used as an internal donor with 15% $TiCl_4$/toluene treatment.

Example 32. Example 9 was repeated except the catalyst treatment was conducted with 20% $TiCl_4$/toluene.

Example 35 demonstrates the preparation of a catalyst component, prepared using an epoxy compound to dissolve $MgCl_2$, and ethyl benzoate. No organosilicon compounds and Al(O-iPr)3 were used. The polymer produced with the catalyst of Example 35, exhibits low bulk density particles and with an irregular morphology.

TABLE 10

Catalyst component characterization (1,3 diether (3,3-bis(methoxymethyl)-2,6-dimethylheptane) (DEMH)

| | D50 | Span | Ti % | Mg % | DEMH, % | CE kg/g | MFR. g/10 mm | XS, % | BD, p/cc | PP D50 | PP Span | B/1.3 | PP morphology |
|---|---|---|---|---|---|---|---|---|---|---|---|---|---|
| Example 30 | 18.4 | 1.014 | | | 19.2 | 76.2 | 8.5 | 1.24 | 0.407 | 835 | 0.620 | 0.736 | Substantially spherical shape |
| Example 31 | 10.8 | 0.525 | 2.66 | 18.03 | 12.2 | 74.6 | 6.8 | | 0.424 | 710 | 1.244 | 0.672 | Rounded raspberry shape |
| Example 32 | 11 | 0.547 | 2.92 | 17.84 | 12.9 | 98.0 | 5.1 | 2.83 | 0.437 | 616 | 1.268 | 0.688 | Rounded raspberry shape |

Example 33. Demonstration of the preparation and performance of the spherical catalyst component. $MgCl_2$(13.2 g), Al(OCH(CH3)2)3 (1.0 g), toluene (59.5 g), tri-n-butylphosphate ("TBP;" 36.3 g), ECH (14.25 g), and Syltherm (6.0 g) are combined and heated to 60° C. with agitation at 600 rpm for 8 hours under a nitrogen atmosphere. Upon cooling to room temperature hexane (59.0 g), dibutyl ether (8 g in 13 g hexane), Viscoplex (6.0 g) in hexane (40 g), and EB (4.5 g) in hexane (5 g) were mixed and cooled to 0° C., at which temperature $TiCl_4$ (288 g) was slowly added with 600 rpm agitation. The temperature was maintained for 1 hour, followed by raising the temperature to 10° C. over 30 minutes, holding for 30 minutes, raising to 85° C. over 70 minutes, and holding for 15 minutes before collecting the solid via filtration. The solid was washed three times with toluene (200 ml) for 10 minutes each at the 85° C. The solid was then collected by filtration and washed with a 10 wt % $TiCl_4$toluene solution (265 ml) with agitation at 85° C., followed by addition of NPDE1 (2.0 g) in toluene (5.0 g) with heating at 85° C. for 60 minute, and followed by filtration. After filtration, the solid was again washed with the $TiCl_4$toluene solution and NPDE1 (0.5 g) in toluene (2 g), but this time at 95° C. After again filtering, the solid was collected, and washed with the TiCldtoluene solution at 110° C. under agitation. Finally, the solid was washed with hexane (200 ml) four times under agitation at 60-65° C., with the catalyst being discharged as a hexane slurry.

Figure 7:
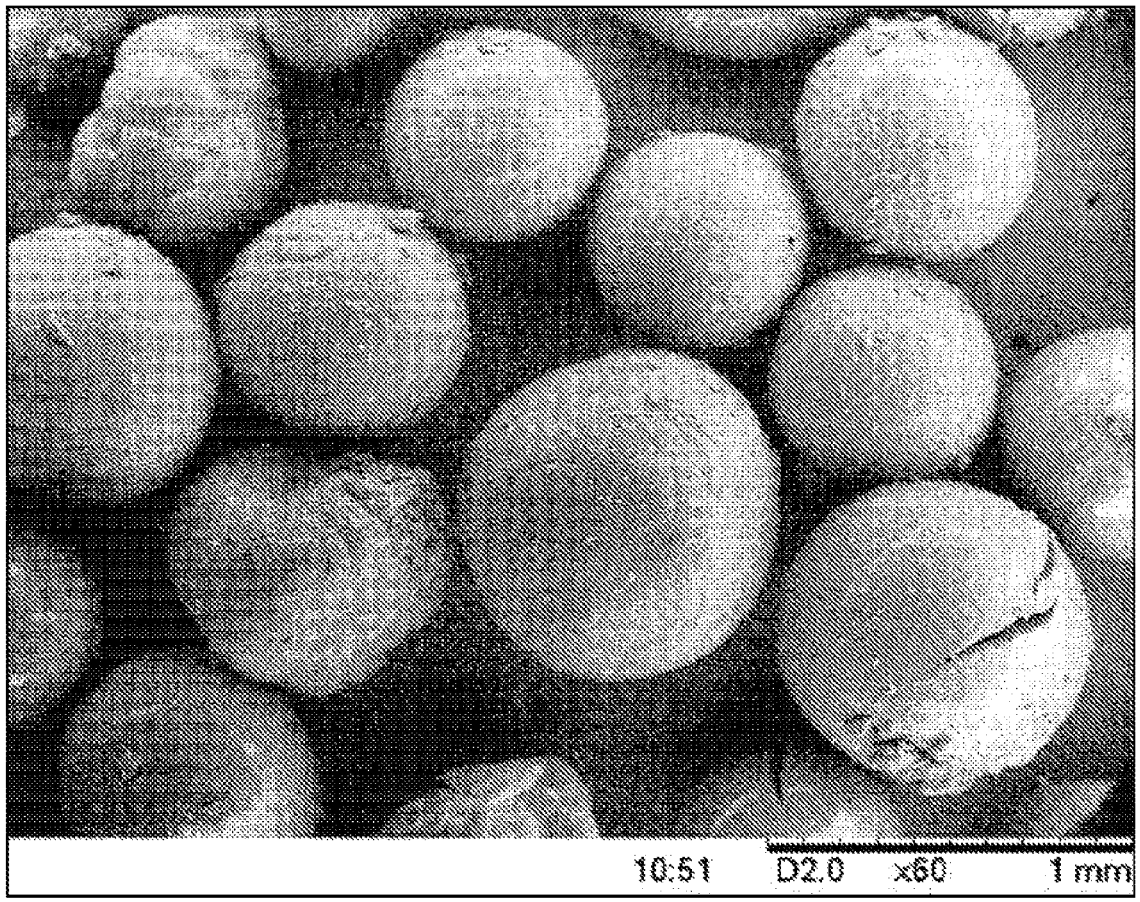
FIG. 7 shows a microscopic view of the polymer produced with the catalyst component of Example 34.

Example 34 demonstrates the preparation of a spherical catalyst component made using epoxy compounds to dissolve $MgCl_2$, but without the use of an anhydride. Instead, an organosilicon compound, Al(O-iPr)3, and ethyl benzoate were used. The polymer produced with this catalyst (FIG. 7) shows high density particles and good sphericity.

Example 35 Demonstration of the preparation and performance of the spherical catalyst component using TEOS instead Syltherm. Example 34 was repeated, however the Syltherm was replaced with TEOS (5 g) and dibutyl ether (12 g) was used.

Example 36 (Comparative). A catalyst was made with EB (no PDMS, no aluminum alkoxide) demonstrating irregular catalyst/polymer morphology, low BD of catalyst/polymer and broad catalyst/PP span. Example 33 was repeated, however no PDMS and Al(OCH(CH3)2)3 were added.

TABLE 11

Analytical Data for the spherical solid catalyst components and polymer properties

| | Example | | |
|---|---|---|---|
| | 34 | 35 | 36 (Comp ) |
| D10 (µ) | 12.6 | 16 9 | 8.6 |
| D50 (µ) | 20.7 | 27.2 | 28.8 |
| D90 (µ) | 34.7 | 44.2 | 60.2 |
| Span | 1.069 | 1.004 | 1.792 |
| Ti% | 1.77 | 2.31 | 2.65 |
| Mg % | 16.23 | 18.50 | 17.23 |
| NPDEI.% | 12.9 | 12.5 | 11.3 |
| CE kg/g | 66.4 | 58.6 | 67.1 |
| MFR. g/10 min | 0.12 | 0.73 | 0.22 |
| XS.% | 1.12 | 1.49 | 1.60 |
| BD. g/ml | 0.439 | 0.390 | 0.387 |
| PP D50 (µ) | 827 | 1098 | 957 |
| PP Span | 0.912 | 0.808 | 1.325 |

Because polymer morphology is a replica of the catalyst morphology, the same trends in the catalyst morphology are expected. The catalyst and polymer morphology are key factors to consider in any commercial polymer production process. It is known that some polymerization processes require good flowability of the polymer, or transfer of the polymer from one reactor unit to another.

The catalysts/methods lead to the production of poly-α-olefins having a a variable molecular weight distribution. Polydispersity Index (PI) is strictly connected with the molecular weight distribution of the polymer.

Examples 37-39 demonstrate properties of polypropylene (PI and rheological breadth) produced with catalyst components using different internal donors

TABLE 12

PI and phelogical breadth of PP produced with selected catalysts

| Example | Catalyst | Internal donor | PI | Rheological Breadth |
|---|---|---|---|---|
| Example 37 | Catalyst based on example 8 | NPDEI | 5.2559 | 0.2754 |
| Example 38 | Catalyst based on example 8 | NPDE1 | 6.1586 | 0.2892 |

TABLE 12-continued

PI and phelogical breadth of PP produced with selected catalysts

| Example | Catalyst | Internal donor | PI | Rheological Breadth |
|---|---|---|---|---|
| Example 39 | Catalyst based on example 31 | DEMH | 3.8113 | 0.3912 |

Example 40-43. The solid catalyst component from example 11 was used for bulk propylene polymerization as described above except a mixture of external donors sold under the designation D6500 were used, which are commercially available from W. R. Grace and Company. The table below demonstrates effect of amount of a mixture of external donors on XS level (catalyst activity) and polymer properties.

TABLE 13

| Example | Catalyst Component | Donor (ml) | Corr CE kg/g | B/D | MFR, g/10 min | XS, % | PP D50, microns | Span | b/13 |
|---|---|---|---|---|---|---|---|---|---|
| Example 40 | Example 15 | 0.39 | 108.8 | 0.411 | 2.46 | 5.53 | 1698 | 1.042 | 0.596 |
| Example 41 | Example 15 | 0.78 | 96.8 | 0.439 | 0.73 | 3.27 | 716 | 1.094 | 0.695 |
| Example 42 | Example 15 | 1.17 | 85.6 | 0.446 | 0.91 | 2.25 | 562 | 0.859 | 0.751 |
| Example 43 | Example 15 | 1.56 | 91.6 | 0.429 | 1.25 | 1.99 | 563 | 0.917 | 0.751 |

The solid catalyst components or the solid precipitates can be used for ethylene polymerization process. Example 44 demonstrates catalyst activity and polyethylene properties produced with solid precipitate from example 15. The polymerization was conducted in hexane in a one-gallon reactor. The reactor was purged at 100° C. under nitrogen for one hour. At room temperature, 0.6 ml of 25-wt % triethylaluminum (TEAL) in heptane was added into the reactor. Then 1500 ml of hexane was added and 10 mg of the catalyst prepared above were added into the reactor. The reactor was pressurized with H2 to 60.0 psig then charged with ethylene to 116 psig. The reactor was heated to and held at 80° C. for two hours. At the end of the hold, the reactor was vented and the polymer was recovered.

TABLE 14

Ethylene polymerization with the solid component

| Example | D50 | Ti, % | Mg, % | CE, kg/g | BD, g/cc | MF12 | MF110 | MF122 | MF1 Ratio | PE D50 | Span |
|---|---|---|---|---|---|---|---|---|---|---|---|
| Example 44 | 12 | 4.45 | 15.84 | 35.2 | 0.303 | 1.918 | 17.205 | 72.484 | 37.791 | 330 | 0.883 |

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. A process of preparing a solid catalyst component for olefin polymerization, the process comprising:
   dissolving a halide-containing magnesium compound in a mixture comprising an epoxy compound, an organic phosphorus compound, and a hydrocarbon solvent to form a homogenous solution;
   treating the homogenous solution with a first titanium compound in the presence of a supportive electron donor to form a solid precipitate;
   treating the solid precipitate with a second titanium compound, optionally in the presence of a non-phthalate electron donor, to form the solid catalyst component;
   wherein:
      the process is free of carboxylic acids and anhydrides;
      the first titanium compound and the second titanium compound are independently represented by:

$Ti(OR)_gX_{4-g}$;

each R is independently a $C_1$-$C_4$ alkyl;
   X is Br, Cl, or I;
   g is 0, 1, 2, or 3;
   the supportive donor comprises an ether, a succinate, a monoaryl ester, a polycarboxylic acid ester, a polyhydroxy ester, a heterocyclic polycarboxylic acid ester, a polyhydroxy ester, a heterocyclic polycarboxylic acid ester, an acrylate, an inorganic acid ester, an alicyclic polycarboxylic acid ester, or a hydroxy-substituted carboxylic acid ester compound having 2 to 30 carbon atoms; and
   the catalyst component comprises particles having a granular, or a substantially spherical or a spherical shape and exhibiting a $D_{50}$ from about 3 μm to about 150 μm.

2. The process of claim 1, wherein the non-phthalate electron donor is different from the supportive donor, and the non-phthalate electron donor comprises an aryl diester, a diether, a succinate, an organic acid ester, a polycarboxylic acid ester, a polyhydroxy ester, a heterocyclic polycarboxylic acid ester, an inorganic acid ester, an alicyclic polycarboxylic acid ester, a hydroxy-substituted carboxylic acid ester compound having 2 to 30 carbon atoms, or a compound having at least one ether group and at least one ketone group, or a mixture of any two or more thereof.

3. The process of claim 1, wherein the non-phthalate electron donor is added prior to or after the solid precipitate is formed, and the process incorporates using two or more the non-phthalate internal donors.

4. The process of claim 1, wherein the process is conducted without the non-phthalate electron donor.

5. The process of claim 1, wherein the treating the homogenous solution is conducted in the presence of a halogenating agent containing at least one halogen atom capable of transfer to the magnesium compound.

6. The process of claim 5, wherein the halogenating agent comprises an aryloyl chloride, an alkanoyl chloride, an alkyl chloride, HCl, $TiCl_4$, $RnTiCl_{4-n}$, $CCl_4$, $R_nSiCl_{4-n}$, or $R_nAlCl_{3-n}$, wherein R is alkyl, cycloalkyl, aryl, or alkoxy, and n is a whole number satisfying the formula 0<n<4 and a ratio of halogenating agent to magnesium compound is at least 1:1 on a mol basis.

7. The process of claim 1, wherein the solid precipitate is formed in presence of a polyacrylate.

8. The process of claim 1, wherein the treating the homogenous solution is conducted in the presence of a di-($C_1$-$C_{12}$)-alkylether.

9. The process of claim 1 wherein the treating of the homogenous solution is conducted in the presence of a hydrocarbon solvent, an aromatic solvent, or a mixture of any two or more thereof.

10. The process of claim 1, wherein the supportive electron donor is represented as:

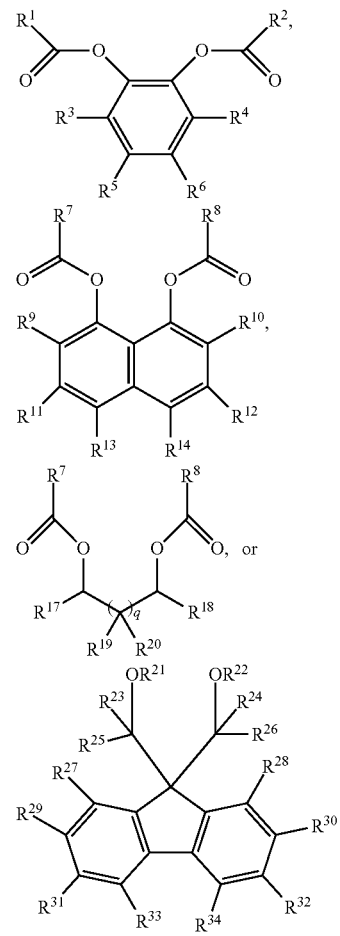

wherein:
   each of $R^1$ through $R^{34}$ is independently H, F, Cl, Br, I, alkyl, cycloalkyl, cycloalkylalkyl, aryl, aralkyl, heterocyclyl, heterocyclylalkyl, heteroaryl, or heteroarylalkyl; and
   q is an integer from 0 to 12.

11. The process of claim 1 wherein the supportive electron donor is methyl formate, butyl formate, ethyl acetate, vinyl acetate, propyl acetate, octyl acetate, cyclohexy acetate, ethyl propionate, methyl butyrate, ethyl butyrate, isobutyl butyrate, ethyl valerate, ethyl stearate, methyl chloroacetate, ethyl dichloroacetate, ethyl acrylate, methyl methacrylate, ethyl crotonate, ethyl cyclohexanecarboxylate, methyl benzoate, ethyl benzoate, propyl benzoate, butyl benzoate, octyl benzoate, cyclohexyl benzoate, phenyl benzoate, benzyl benzoate, ethyl p-methoxybenzoate, methyl p-methylbenzoate, ethyl p-t-butylbenzoate, ethyl naphthoate, methyl toluate, ethyl toluate, amyl toluate, ethyl ethylbezoate, methyl anisate, ethyl anisate, ethyl ethoxybenzoate, or a mixture of any two or more thereof.

12. The process of claim 1, wherein the epoxy compound is a glycidyl-containing compound represented by Formula:

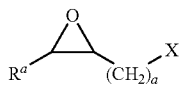

wherein:
a is 1, 2, 3, 4, or 5;
X is alkyl, F, Cl, Br, I; and
$R^a$ is H, alkyl, aryl, or cyclyl.

13. The process of claim 1, wherein the organic phosphorus compound is represented as:

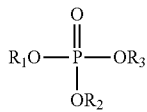

wherein: $R_1$, $R_2$, and $R_3$ are each independently C1-C10 alkyl.

14. The process of claim 1, wherein an organosilicon compound is added during the process and the organosilicon compound contains O—Si—O, Si—O—Si groups, or both O—Si—O and Si—O—Si groups.

15. The process of claim 14 wherein the organosilicon compound is a silane, siloxane or polysiloxane represented as:

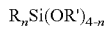

wherein:
each R is H, alkyl, or aryl;
each R' is H, alkyl, aryl, or a $SiR_n(OR')_{3-n}$; and
n is 0, 1, 2, or 3.

16. The process of claim 1, wherein the halide-containing magnesium halide compound is magnesium chloride.

17. A polymerization process comprising polymerizing an olefin in the presence of the solid catalyst component produced according to the process of claim 1, an organoaluminum compound, and, optionally, an external electron donor, an activity limiting agent, or both an external electron donor and an activity limiting agent.

18. A process for polymerizing or copolymerizing an olefinic monomer, the process comprising contacting an olefinic monomer, and optionally a comonomer, with the solid catalyst component produced according to the process of claim 1, an organoaluminum compound, and at least one selectivity control agent to form a polyolefin, wherein the at least one selectivity control agent comprises a silane compound, and, optionally, an activity limiting agent.

19. The process of claim 18, wherein the polyolefin comprises polymer particles having a granular, a substantially spherical shape, or a spherical shape, and exhibiting an aspect ratio B/L3 greater than about 0.6.

* * * * *